US012749578B2

(12) United States Patent
Hwang et al.

(10) Patent No.: US 12,749,578 B2
(45) Date of Patent: Sep. 29, 2026

(54) SYSTEMS AND METHODS FOR USER AUTHENTICATION IN VIDEO COMMUNICATIONS

(71) Applicant: Polyview Health, Inc., San Diego, CA (US)

(72) Inventors: Jason Hwang, Henderson, NV (US); Gregory Deocampo, Safety Harbor, FL (US); Dimitri Arges, Henderson, NV (US)

(73) Assignee: Polyview Health, Inc., Menlo Park, CA (US)

( * ) Notice: Subject to any disclaimer, the term of this patent is extended or adjusted under 35 U.S.C. 154(b) by 277 days.

(21) Appl. No.: 18/746,149

(22) Filed: Jun. 18, 2024

(65) Prior Publication Data

US 2024/0428432 A1 Dec. 26, 2024

Related U.S. Application Data

(60) Provisional application No. 63/604,930, filed on Dec. 1, 2023, provisional application No. 63/510,608, filed
(Continued)

(51) Int. Cl.
*G16H 40/67* (2018.01)
*G06F 3/0484* (2022.01)
(Continued)

(52) U.S. Cl.
CPC ........... *G16H 40/67* (2018.01); *G06F 16/635* (2019.01); *G06F 21/32* (2013.01); *G06F 40/35* (2020.01);
(Continued)

(58) Field of Classification Search
CPC ...... G06V 10/82; G06V 40/172; G06V 10/44; G06V 40/168; G16H 10/60; G16H 40/67;
(Continued)

(56) References Cited

U.S. PATENT DOCUMENTS 10,984,545 B2 * 4/2021 Gu .......................... G06N 3/08
11,861,788 B1 * 1/2024 Taghavi Nasrabadi ...................... G06T 15/08
(Continued)

FOREIGN PATENT DOCUMENTS

WO WO-2018170393 A2 * 9/2018 ........... G06T 3/4046

OTHER PUBLICATIONS

International Search Report and Written Opinion mailed Oct. 9, 2024 in International Application PCT/US2024/034813.
(Continued)

*Primary Examiner* — Mia M Thomas

(57) ABSTRACT

Systems and method are provided for authenticating a user of a communication session. A computing device may receive a video frame from a communication session between a first user device and a second user. The computing device may extract at features from the video frame and execute a neural network using the set of features. The neural network may be configured to generate a depth map of a user represented in the video frame. The computing device may authenticate a user of the first user device by matching the depth map to a second depth map associated with an authenticated user. Upon authenticating the user, the computing device may generate a third depth map by merging the depth map with the second depth map. The third depth map may be used to authenticate the user during a subsequent communication session involving the user.

20 Claims, 5 Drawing Sheets

Related U.S. Application Data on Jun. 27, 2023, provisional application No. 63/510,019, filed on Jun. 23, 2023, provisional application No. 63/510,006, filed on Jun. 23, 2023, provisional application No. 63/509,973, filed on Jun. 23, 2023, provisional application No. 63/509,910, filed on Jun. 23, 2023.

(51) Int. Cl.

| | |
|---|---|
| ***G06F 16/635*** | (2019.01) |
| ***G06F 21/32*** | (2013.01) |
| ***G06F 40/35*** | (2020.01) |
| ***G06F 40/58*** | (2020.01) |
| ***G06N 3/0455*** | (2023.01) |
| ***G06N 3/0475*** | (2023.01) |
| ***G06T 7/50*** | (2017.01) |
| ***G06V 10/44*** | (2022.01) |
| ***G06V 40/16*** | (2022.01) |
| ***G16H 80/00*** | (2018.01) |
| ***H04L 12/18*** | (2006.01) |
| ***H04L 65/1069*** | (2022.01) |
| ***H04L 65/1083*** | (2022.01) |
| ***H04L 67/306*** | (2022.01) |

(52) U.S. Cl.

CPC ........... *G06F 40/58* (2020.01); *G06N 3/0455* (2023.01); *G06N 3/0475* (2023.01); *G06T 7/50* (2017.01); *G06V 10/44* (2022.01); *G06V 40/168* (2022.01); *G16H 80/00* (2018.01); *H04L 12/1831* (2013.01); *H04L 65/1069* (2013.01); *H04L 65/1083* (2013.01); *H04L 67/306* (2013.01); *G06F 3/0484* (2013.01); *G06T 2207/20084* (2013.01)

(58) Field of Classification Search

CPC ....... G16H 80/00; G06F 16/635; G06F 21/32; G06F 40/35; G06F 40/58; G06F 3/0484; G06N 3/0455; G06N 3/0475; G06N 3/045; G06N 3/047; G06N 20/00; G06T 7/50; G06T 2207/20084; H04L 12/1831; H04L 65/1069; H04L 65/1083; H04L 67/306

See application file for complete search history.

(56) References Cited

U.S. PATENT DOCUMENTS

| | | | | |
|---|---|---|---|---|
| 11,871,123 | B2 * | 1/2024 | Zhang | H04N 23/676 |
| 12,387,503 | B2 * | 8/2025 | Ambrus | G06V 10/774 |
| 2014/0195255 | A1 | 7/2014 | Ghosh et al. | |
| 2014/0214443 | A1 | 7/2014 | Duffy et al. | |
| 2015/0120293 | A1 | 4/2015 | Wohlert et al. | |
| 2015/0172607 | A1 | 6/2015 | Manber | |
| 2016/0323546 | A1 * | 11/2016 | Hines | H04N 13/167 |
| 2017/0011740 | A1 | 1/2017 | Gauci | |
| 2017/0344726 | A1 | 11/2017 | Duffy et al. | |
| 2017/0374269 | A1 * | 12/2017 | Govindarao | H04N 23/959 |
| 2018/0359530 | A1 | 12/2018 | Marlow et al. | |
| 2019/0385711 | A1 | 12/2019 | Shriberg et al. | |
| 2020/0026831 | A1 | 1/2020 | Alameh et al. | |
| 2020/0253527 | A1 | 8/2020 | Ellison | |
| 2020/0312428 | A1 | 10/2020 | Reeves et al. | |
| 2021/0027480 | A1 * | 1/2021 | Ren | G06N 3/084 |
| 2021/0058472 | A1 | 2/2021 | Wylie et al. | |
| 2021/0065703 | A1 | 3/2021 | Maeng et al. | |
| 2021/0287469 | A1 | 9/2021 | Ryhorchuk et al. | |
| 2021/0312184 | A1 | 10/2021 | Olshansky | |
| 2021/0344675 | A1 | 11/2021 | Cui et al. | |
| 2022/0237368 | A1 | 7/2022 | Tran | |
| 2022/0286657 | A1 | 9/2022 | Oz et al. | |
| 2022/0374585 | A1 | 11/2022 | Wang et al. | |
| 2025/0069247 | A1 * | 2/2025 | Ren | G06T 7/194 |

OTHER PUBLICATIONS

International Search Report and Written Opinion mailed Aug. 20, 2024 in International Application PCT/US2024/034775.

International Search Report and Written Opinion mailed Sep. 16, 2024 in International Application PCT/US2024/034650.

International Search Report and Written Opinion mailed Sep. 19, 2024 in International Application PCT/US2024/035157.

International Search Report and Written Opinion mailed Sep. 20, 2024 in International Application PCT/US2024/034818.

International Search Report and Written Opinion mailed Sep. 30, 2024 in International Application PCT/US2024/034811.

* cited by examiner

| Feature ID | Distance (mm) |
| --- | --- |
| 304 | 762 |
| 308 | 764 |
| 312 | 759 |
| 316 | 761 |
| 320 | 763 |
| ... | ... |

| Feature IDs | Abs Delta (mm) |
| --- | --- |
| 304 to 308 | 2 |
| 304 to 312 | 3 |
| 304 to 316 | 1 |
| 304 to 320 | 1 |
| 308 to 312 | 5 |
| ... | ... |

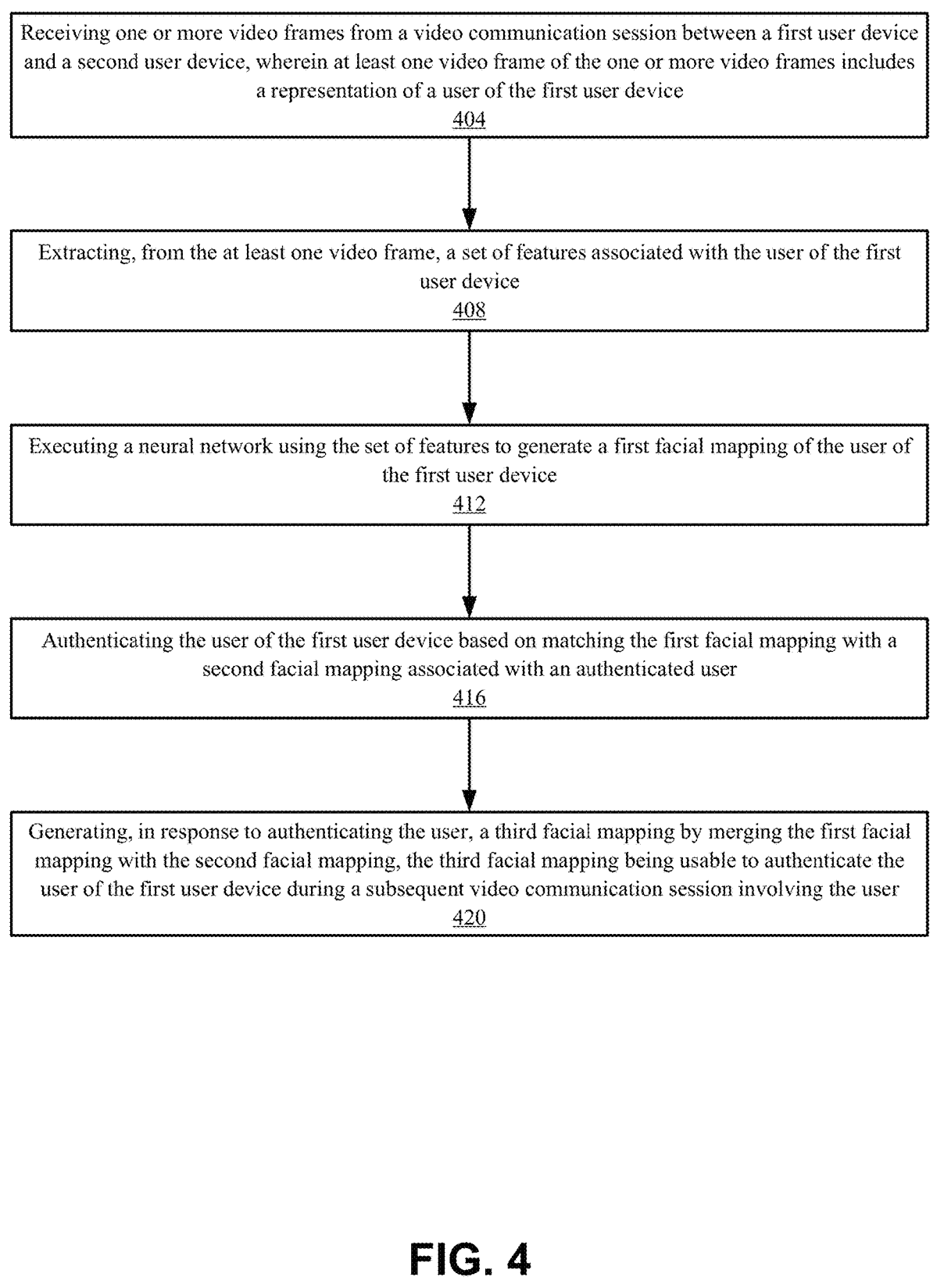

Receiving one or more video frames from a video communication session between a first user device and a second user device, wherein at least one video frame of the one or more video frames includes a representation of a user of the first user device
404

Extracting, from the at least one video frame, a set of features associated with the user of the first user device
408

Executing a neural network using the set of features to generate a first facial mapping of the user of the first user device
412

Authenticating the user of the first user device based on matching the first facial mapping with a second facial mapping associated with an authenticated user
416

Generating, in response to authenticating the user, a third facial mapping by merging the first facial mapping with the second facial mapping, the third facial mapping being usable to authenticate the user of the first user device during a subsequent video communication session involving the user
420

FIG. 4

SYSTEMS AND METHODS FOR USER AUTHENTICATION IN VIDEO COMMUNICATIONS

CROSS-REFERENCE TO RELATED APPLICATIONS

The present patent application claims the benefit of priority to U.S. Provisional Patent Applications 63/509,910, 63/509,973, 63/510,006, and 63/510,019, all of which were filed Jun. 23, 2023; U.S. Provisional Patent Application 63/510,608, filed Jun. 27, 2023; and U.S. Provisional Patent Application 63/604,930, filed Dec. 1, 2023, which are all incorporated herein by reference in their entirety for all purposes.

TECHNICAL FIELD

This disclosure relates generally to authenticating users of a communication session, and more particularly to authenticating users of a communication session by identifying users using face and/or voice features.

BACKGROUND

Telemedicine may enable healthcare providers to increase access to health services by providing healthcare services over various remote channels (e.g., telephone, video conference, chat services, etc.). Patients may receive healthcare from any location without being physically present in a doctor's office or nearby to a doctor. Although the use of telemedicine can increase access to healthcare, telemedicine may make some forms of healthcare fraud easier. For instance, some fraudulent actors (e.g., doctors with revoked medical licenses, forged medical licenses, etc.) may impersonate a doctor to commit medical insurance fraud, steal patient information, attempt to obtain money from the patient, etc. A remote patient may have limited or no experience with a particular doctor and, as a result, may not know whether the doctor connected to the telemedicine session is a real doctor or a fraudulent actor. Furthermore, some generative artificial intelligence algorithms may be capable of modifying a portion of the video and/or audio of a telemedicine session to cause a fraudulent actor to appear as an authenticated doctor.

SUMMARY

Methods are described herein for authenticating a user of a communication session. The methods may include receiving one or more video frames from a video communication session between a first user device and a second user device, wherein at least one video frame of the one or more video frames includes a representation of a user of the first user device; extracting, from the at least one video frame, a set of features associated with the user of the first user device; executing a neural network using the set of features to generate a first depth map of the user of the first user device; authenticating the user of the first user device based on matching the first depth map with a second depth map associated with an authenticated user; and generating, in response to authenticating the user, a third depth map by merging the first depth map with the second depth map, the third depth map being usable to authenticate the user of the first user device during a subsequent video communication session involving the user.

Systems are described herein for authenticating a user of a communication session. The systems may include one or more processors and a non-transitory computer-readable medium storing instructions that, when executed by the one or more processors, cause the one or more processors to perform any of the methods as previously described.

The non-transitory computer-readable media described herein may store instructions which, when executed by one or more processors, cause the one or more processors to perform any of the methods as previously described.

These illustrative examples are mentioned not to limit or define the disclosure, but to aid understanding thereof. Additional embodiments are discussed in the Detailed Description, and further description is provided there.

BRIEF DESCRIPTION OF THE DRAWINGS

Features, embodiments, and advantages of the present disclosure are better understood when the following Detailed Description is read with reference to the accompanying drawings.

FIG. 4 illustrates a flowchart of an example process authenticating users connected to a communication system according to aspects of the present disclosure.

DETAILED DESCRIPTION

Figure 1:
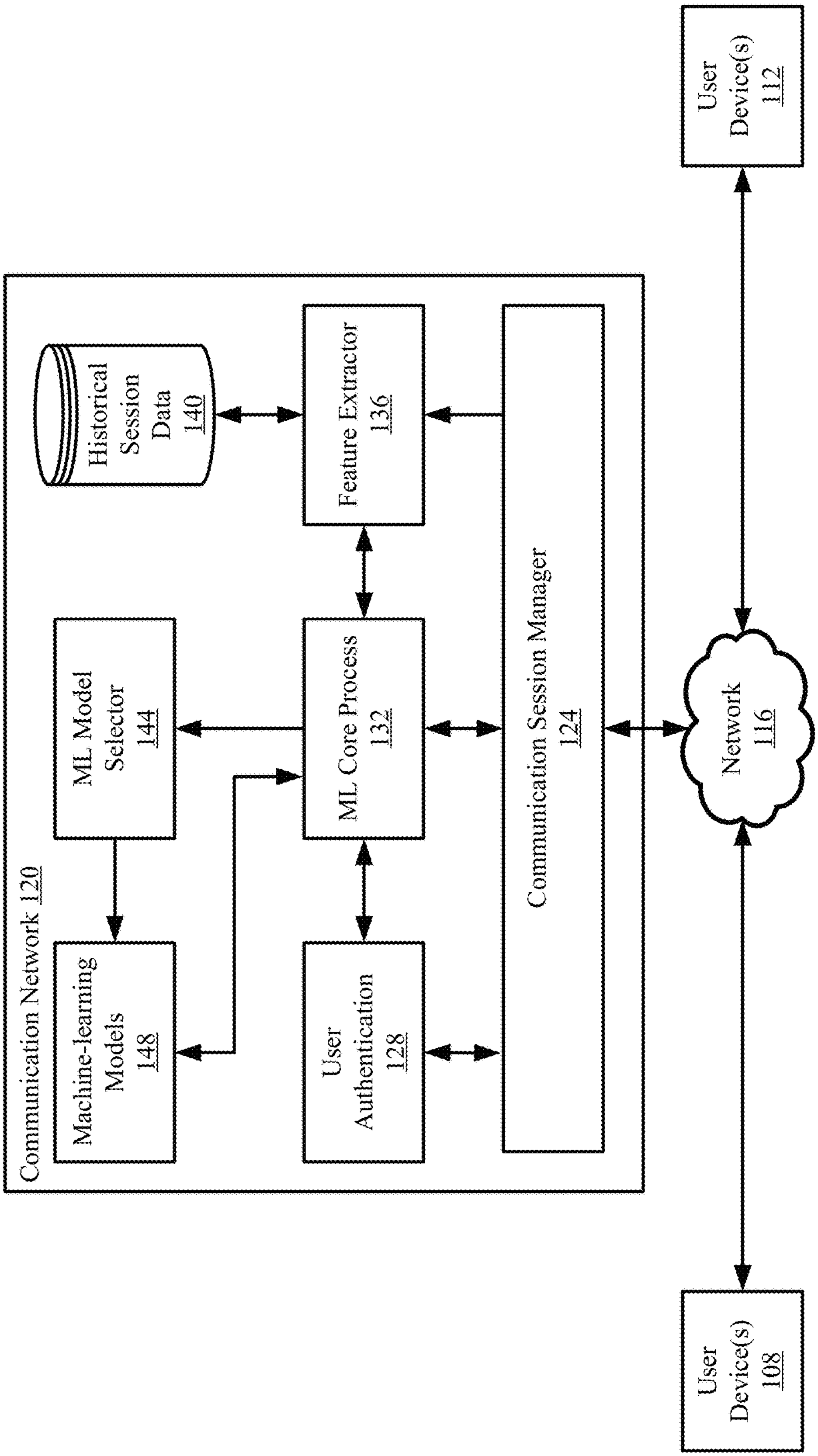
FIG. 1 illustrates a block diagram of example communication network configured to facilitate secured communication sessions between users according to aspects of the present disclosure.

Method and systems are described herein for authenticating users of a communication session. In some examples, the communication session may be a telemedicine session in which the users include one or more patients, one or more individuals associated with the one or more patients (e.g., children, parents, nurses, social workers, aides, etc.) and one or more healthcare providers. The communication session can be facilitated by a communication system configured to authenticate the users of the communication in real time based on access credentials, communications transmitted over the communication session, metadata including in the communications, combinations thereof, or the like. For example, the communication system may use facial and/or vocal information associated with a user and compare it to historical facial and/or vocal information previously obtained from the user to determine that the facial and/or vocal information is from the same user. The communication system may authenticate users at the beginning of the communication session and/or in regular intervals throughout the communication session (e.g., to prevent an unauthorized user from impersonating an authorized user after the initial authentication). By ensuring that the users of the communication session correspond to known users, the communication session can prevent unauthorized users from impersonating other users and taking advantage of users or the communication session.

The communication session may be configured to authenticate users using information associated with the user that may be obtained through the communication system or during the communication session. The information may include personal identifiable information (PII) that may be usable alone or with other information to determine the identity of the user. The information may be obfuscated by using, for example, a hash function, salting, feature selection, combinations thereof, or the like to generate a set of obfuscated features that may not be usable to derive an identity of the user. The set of obfuscated features may be configured to prevent reconstruction of user identifiable information or characteristics (e.g., physical characteristics, voice characteristics, etc.) of the user. The obfuscated features cannot be used to derive the information associated with the user that were used to generate the obfuscated features. The obfuscated features, though derived from personal identifiable information, may not be considered personal information.

For example, the communication network may facilitate a communication session using bi-directional, audiovisual software. The communication session may extract one or more frames from a first user device operated by a healthcare provider. The one or more frames may include a representation of the healthcare provider (e.g., such as the healthcare providers face, etc.). The communication network may then derive obfuscated features from the one or more frames that uniquely represent the healthcare provider but cannot be used to reconstruct the representation of the healthcare provider. For example, the communication network may use one or more machine-learning models to identify facial features from the representation of the healthcare provider. In some examples, the facial features may be an estimate distance between a pixel of the frame representing of the healthcare provider and the camera of the first user device (e.g., such as monocular depth estimation, etc.). The communication network may determine the relative differences between the one or more facial features to derive a map of the healthcare provider. The communication network may limit the quantity of facial features identified or may discard one or more facial features (e.g., such as facial features that may increase a likelihood of enabling reconstruction of the representation of the healthcare provider or facial features that may be less usable, etc.) to prevent reproducing the representation of the healthcare provider). The obfuscated features may include the remaining facial features.

The communication network may also derive obfuscated features from audio segments comprising a representation of a voice of the healthcare provider. The communication network may isolate audio segments from the first user device. The audio segments may be of any length such as but not limited to 1 second, 5 seconds, 10 seconds, etc. In some instances, the length of the audio segment may be determined by a quantity of words spoken in the audio segment (e.g., as determined by frequency or amplitude analysis, a machine-learning model, combinations thereof, or the like). The audio segment may be processed to improve feature extraction from the audio segment. Preprocessing the audio segment may include passing the audio segment through a band-pass filter (to eliminate particular frequency ranges associated with noise), or the like. The preprocessed audio segment may then be passed through a machine-learning model (e.g., such as recurrent neural network, classifier, or the like) to derive features usable to determine a likelihood that the representation of a voice of the healthcare provider corresponds to an authorized healthcare provider. The machine-learning model may use frequency analysis (e.g., to identify if the audio segment uses similar frequencies as used by the healthcare provider), pattern analysis (e.g., speech rate, consistent pronunciation, consistent pausing, etc.), word choice analysis (e.g., consistent vocabulary, etc.), combinations thereof, or the like. The output from the machine-learning model is a set of values corresponding to each analysis performed on the audio segment.

The communication network may derive other features from the communication session that may be usable to determine if the first user device is being operated by an authenticated user (e.g., a real healthcare provider). For example, the communication network may extract information such as, but not limited to, device information (e.g., hardware components and/or software installed on the first user device), network information (e.g., Internet Protocol (IP) address, Media Access Control (MAC) address, etc.), configuration information (e.g., a configuration of the communication session, etc.), a start date and/or time of the communication session, a timestamp corresponding to when the first user device connected to the communication session relative to the date and/or time of the communication session (e.g., to determine when the first user device connected to the communication session relative to when the communication session is expected to begin), combinations thereof, or the like. The other features may be usable to determine whether the first user device corresponds to a same user device previously operated by the healthcare provider, whether the first user device is operating from a same location as previously operated by the healthcare provider, whether the user of the first user device configured the communications in a same or similar manner as the healthcare provider previously configured communication sessions, whether the user of the first user device connected to the communication session relative to the communication session start time in a similar manner as the healthcare provider, etc.

The communication session may obfuscate and/or remove some of the extracted information to prevent storing or processing information that may identify the healthcare provider. For example, for extracted information that can be directly compared to previously stored data (e.g., such as an IP address, hardware components or software installed on the first user device, etc.) and that may be usable to identify the healthcare provider (e.g., such as an IP address, etc.), the communication network may hash the extracted information. Identical information hashed using a same hashing function will generate a same hash value. If two hash values are identical, then the data from which the hash values were generated are also identical. Hashing may enable the communication network to use a representation of personal identifiable information for authentication without exposing the personal identifiable information. The communication network may discard extracted information that cannot be directly compared and that may be usable to identify the healthcare provider.

The set of obfuscated features extracted from a communication session may be determined based on the commination channel of the communication session. For example, for audiovisual communications, the set of obfuscated features may include obfuscated features derived from the one or more frames, obfuscated features derived from audio segments, and/or the other features derived from the communication session. For audio communications, the obfuscated features may include obfuscated features derived from audio segments, and/or the other features derived from the communication session. The obfuscated features included in the set of obfuscated features may also be determined by a machine-learning model (e.g., configured for feature extraction, etc.), one or more configuration parameters, user input, the first user device, and/or the like.

The set of obfuscated features may be stored in a secured data structure that is continuously updated and historically persistent. In some instances, the secured data structure may store data in a set of immutable nodes. The set of nodes may be organized into a sequence based on the time in which the node was generated. A first node may be generated at a first time that obfuscated features are derived for a particular user. The first node may store a dataset including a representation of the obfuscated features (e.g., the obfuscated features themselves, an output of one or more machine-learning models that processed the obfuscated features, and/or the like), a timestamp corresponding to when the obfuscated features were generated, metadata associated with the obfuscated features, etc. In some instances, the dataset may be encrypted to prevent unauthorized access to the dataset. The dataset may be encrypted as a whole or may be encrypted in chunks using different encryption algorithms, different keys, or the like.

Since there is no previous data to compare the first node to, the communication network may verify the authorization status of the particular user associated with the first node using one or more other security measures. Examples of such security measures include matching tokens (e.g., such as a token issued to the particular by the communication network using a different communication channel to a corresponding token of the communication network), cryptographic keys, matching hashes (e.g., matching hash generated by the communication network to a hash generated by a device associated with the particular user), manual authentication (e.g., using a user of the communication network to authenticate the particular user), knowledge-based authentication (KBA), combinations thereof, or the like. In some instances, the first node may not be compared to any other information sources. If the first node is associated with any authorized access, operations, or the like, the first node may be used to prevent the particular user from accessing the communication network again.

When new obfuscated features are derived from a user identified as the particular user, the communication network may generate a new dataset (e.g., including the newly derived obfuscated features, a new timestamp corresponding to when the newly derived obfuscated features were generated, metadata associated with the newly derived obfuscated features, etc.) and compare the new dataset to the dataset of the first node (or the most recently generated node). The communication system may use one or more comparison algorithms to determine whether the new dataset is sufficiently similar so as to correspond to the same particular user within a reasonable margin of error. For example, the communication system may use a vector distance (e.g., measuring a distance between corresponding data of the new dataset and the data of the first node in an n-dimensionality representation space), Boolean comparison (e.g., direct true or false matching of corresponding data of the new dataset and the data of the first node), combinations thereof, or other comparison algorithms. If the communication network determines that the new dataset and the dataset of the first node correspond to the same user (e.g., the particular user), then the communication network may generate a second node and generate a third dataset to store in the second node. The third dataset may be generated by merging the obfuscated features of the new dataset with the obfuscated features of the dataset of the first node. The third dataset may include the timestamp of the second dataset, the metadata of the dataset of the first node, and the metadata of the new dataset. The third dataset may be stored in the second node along with a link (e.g., such as pointer, etc.) to the first node.

Each time a new set of obfuscated features are derived from a user identified as the particular user, the communication network may generate (upon determining that the new obfuscated features and the dataset of the most recently generated node correspond to the same particular user) a new node, store a new third dataset in the new node, and link the new node to the immediately previously generated node (e.g., based on time, etc.). The most recently generated node may store a third dataset that corresponds to an aggregated representation (e.g., such as a concatenation, average, or the like) of the obfuscated features of each previous node of the secured data structure. By generating aggregated representations, aspects of the user operating the first user device that are subject to high degrees of variability across communication sessions (e.g., changes in clothing, hair style, backgrounds, lighting, etc.) may be deemphasized. This may prevent a small variation in the representation of the user of the first user device (e.g., such as different clothing, etc.) from being interpreted as a new or different user.

The communication network (or an administrator thereof) may search secured data structures associated with users of the communication network to ensure that the users of the communication network correspond to the verified, authenticated users. Since the secured data structures store obfuscated features (rather than personal identifiable information), users can be authenticated without handling (e.g., storing, processing, transmitting, comparing, etc.) personal identifiable information. If a secured data structure is compromised, no personal identifiable information will be accessible. The communication network may delete a secured data structure if comprised and generate a new one next time the user associated with the deleted secured data structure access the communication network.

Once a node is generated and a third dataset is stored within the node, the communication network may ensure the node remains persistent as long as the corresponding secured data structure remains. For example, the communication network may generate partial or complete hashes, checksums, or the like using a third dataset of a node. The hashes, checksums, or the like may be usable by the communication network to determine if the node has been modified in any way. If so, the node may be removed from the secured data structure and the previous node in the set of nodes may be linked to the subsequent node in the set of nodes if present. Alternatively, or additionally, the secured data structure may be stored in a write protected region of memory such as a read-only memory, memory protection (e.g., segmentation, protection keys, protection rings, etc.), where the nodes of the secured data structure cannot be altered once stored.

In some instances, the secured data structure may be a blockchain or non-distributed ledger in which each node may be a block of the blockchain or ledger. In other instance, the secured data structures may be stored as individual data structure (e.g., each node being a distinct data structure) in a database or other storage structure.

In an illustrative example, a communication network may receive one or more video frames from a video communication session between a first user device and a second user device. The first user device may be operated by a healthcare provider and the second user device may be operated by patient. One or more other devices may also be connected to the communication session operated by users that may be affiliated with the healthcare provider (e.g., such as an administrator, another healthcare provider, nurse, aide, etc.) or the patient (e.g., such a guardian, nurse, aide, etc.). The communication network may authenticate any user connected to the communication session. In some instances, the communication network may authenticate each user other than the patient (to preserve the patient's privacy and/or to prevent gathering or storing sensitive information associated with the patient). In other instances, the communication network may authenticate each user connected to the communication session.

The communication network may authenticate users using the one or more video frames (at least one of which may include a representation of a user). The first user device and the second user device may each include a camera facing the user of the first user device and the second user device. The camera may capture a single video frame (e.g., an image or the like), periodically capture video frames, or continuously capture video frames as part of the communication session. The communication network may use the video frames to authenticate the user.

The communication network may extract, from at least one video frame, a set of features associated with the user of the first user device. The features may correspond to characteristics of the video frame and/or the communication from which the video frame was received (e.g., such as characteristics of the user device, network information associated with the user device, etc. as previously described). In some examples, the set of features correspond to a preprocessed version of the video frame in which portions of the video frame that do not represent a human person are omitted.

The communication network may execute a neural network using the set of features to generate a first depth map of the user of the first user device. Alternatively, the communication network may execute the neural network using the one or more video frames. The first depth map may be a depth map that defines a distance value for each pixel of the video frame that corresponds to an estimated distance of the point in the environment represented by the pixel is from the camera that captured the video frame. The depth map may provide a representation of a face of the user represented in the video frame. The depth map may be normalized by deriving the relative differences between a distance value and one or more other distance values. For example, the communication network may select the smallest depth value (e.g., the pixel representing a point estimated to be closest to the camera) and deriving, for each depth value the absolute difference from the smallest depth value. By normalizing the depth map, the communication network can derive a version of the depth map that is unaffected by the distance of the user from the camera.

The communication network may authenticate the user of the first user device based on matching the first depth map with a second depth map associated with an authenticated user. The communication network may store user profiles associated with authenticated and non-authenticated users. The user profile may store a sequence of nodes as a linked data structure (e.g., digital ledger such as a blockchain, linked list, etc.), where each node stores a minimized depth map (e.g., minimized version of a normalized depth map) and linked to previously generated node. The communication network may compare the first depth map to the depth map of the first node in the sequence of nodes (e.g., the most recently generated node). If the two depth maps match (e.g., determined using a distance algorithm, a machine-learning model, etc.), communication network may determine that the user of the first user device is the same user as the user associated with the user profile. If the user profile corresponds to an authenticated user, then the user of the first user device may be determined to be an authenticated user.

The communication network may generate a new node in the sequence of nodes that includes a depth map generated from the first depth map and the depth map that was stored in the first node. The new node may become the new most recently generated node and used during subsequent comparisons involving the user profile. Since the user profile is updated each time a match is detected, the depth maps of the user profile may more accurately correspond to the user over time (e.g., increasing accuracy and reducing false positives and false negatives).

The minimized depth map may be generated by generating a depth map (or normalized depth map) and systematically removing distance values until a minimum quantity of distance values remain. The minimized depth map may be generated to prevent storing personal identifiable information or other information that may be sensitive to the user associated with the user profile. Removing distance values from a depth map may increase a likelihood that a first depth map from more than one user may match a same minimized depth map. The communication network may use user input, previous iterations of the authentication process, one or more machine-learning models (e.g., cluster-based models, autoencoders, etc.), feature importance, etc.) to determine a minimum quantity of distance values to authenticate a particular user based on comparing one or more other features associated with the user (e.g., such as other objects in the video frame, voice-pattern analysis of the user, user device characteristics, network characteristics associated with the user device such as an IP address, etc.). Generally, the larger the quantity of other features available to compare, the fewer depth values needed to authenticate the user (relative to a predetermined minimum quantity of depth values). For example, the first depth map may be matched to the second depth map (e.g., the minimum depth map), which as a result of the removal of one or more depth values may also be matched to depth maps of one or more other users. The communication network may increase the accuracy of the matching by also matching an IP address of the first user device to ensure that the user of the first user device is likely the user associated with the authenticated user profile. The communication network may use any feature that can be extracted from the first user device during the communication session (e.g., video frames, characteristics of the first user device characteristics, characteristics of a network connection of the first user device, user credentials, cryptographic keys, tokens, codewords, etc.).

By matching the first depth map to the (minimized) second depth map, the communication network can authenticate users without storing or exposing personal identifiable information (e.g., such as, but not limited to, images or other representations of the user).

The communication network may generate, in response to authenticating the user, a third depth map by merging the first depth map with the second depth map. The third depth map may be used to authenticate the user of the first user device during a subsequent video communication session involving the first user. The first depth map may be merged with the second depth map calculating an updated distance value for each distance value of the second depth map based on the first depth map. The second depth map (e.g., the minimized depth map) may include a second set of distance values with each distance value being associated with an approximate location (e.g., coordinate location, facial region, or the like) of a representation of the user (e.g., such as a face of the user, etc.) associated with the second depth map. The communication network may identify a first set of distance values from the first depth map associated with a same location as the distance values of the second depth map (e.g., each distance value of the first set of distance values may be a distance value associated with a same location as a corresponding distance value of the second depth map). The communication network may then define a third set of distance values with each distance value of the third set of distance values derived based on a distance value of the second set of distance values and the corresponding distance value of the first set of distance values (e.g., the distances values of the first set of distance values and the second set of distance values representing a same location of the representation of the user). The third set of distance values may be derived based on deriving an aggregation of the distance values (e.g., appending the distance values, adding the distance values, etc.), average of the distance values, median of the distance values, mode of the distance values, another statistical merging process, combinations thereof, or the like. In some instances, the communication network may store the distance values each set of distance values evaluated to enable generating update sets of distance values each time the user is authenticated.

The third depth map (e.g., the third set of distance values) may be used to generate a new node of the matched user profile usable to authenticate the user during the communication session and/or during a subsequent communication session. When the user of the first user device connects to a subsequent communication session, the communication network may generate a new depth map and compare the new depth map to the third depth map of the user profile. Each time the user profile is matched to a depth map of a user, the user profile may be updated generating a new node and a new (minimized) depth map. Over time the depth map of the user profile may be less subject to small variations in distances, increasing the accuracy of the depth map.

FIG. 1 illustrates a block diagram of example communication network configured to facilitate secured communication sessions between users according to aspects of the present disclosure. Communication network 120 may facilitate communication sessions between a first user device operated by a patient (e.g., user device 108) and a second user device operated by a healthcare provider (e.g., user device 112). Communication network 120 may enable one or more other devices associated with the first user device (e.g., such as nurses, aides, social workers, parents, adult children, etc.) and/or the second user device (e.g., nurses, assistants, other doctors, administrators, etc.) to connect to the communication session.

Communication network 120 may include one or more processing devices (e.g., computing devices, mobile devices, servers, databases, etc.) configured to operate together to provide the services of communication network 120. The one or more processing devices may operate with a same local network (e.g., such as a local area network, wide area network, mesh network, etc.) or may be distributed processing devices (e.g., such a cloud network, distributed processing network, or the like). User device 108 and user device 112 may connect to communication network 120 directly or through one or more intermediary networks 116 (e.g., such as the Internet, virtual private networks, etc.).

The first user device or the second user device may request a new communication session using communication session manager 124. The request may include an identification of one or more user devices are authorized to connect to the communication session. The request may also include other parameters such as user profile data (associated with the first user device or the second user device, such as, but not limited to an identification of a user of the user profile, a user identifier, user devices operated by the user), a purpose for establishing the communication session, a start time of the communication session, an expected duration of the communication session, settings of the communication session (e.g., audio channel settings, video channel settings, collaborative window settings, wrapper settings, etc.), combinations thereof, or the like.

Communication session manager 124 may then instantiate a new communication session for the first user device and/or the second user device. Communication session manager 124 may authenticate each user device that connects to the new communication session using user authentication 128. User authentication 128 may ensure that the user of a connected user device corresponds to an authorized user. To avoid exposing personal identifiable information or medical information, user authentication 128 may compare obfuscated features associated with the user to corresponding obfuscated features associated with an authorized user. In some instances, the obfuscated features may include an obfuscated representation of a username, password, token, public/private key, and/or the like. Communication session manager 124 may distribute passwords, tokens, public/private keys, and/or the like with an invitation to connect to the new communication session. In some instances, the obfuscated features may include biometric features of a user of a user device to be authenticated such as physical features, vocal features, and/or the like.

User authentication 128 may obtain one or more video frames and/or one or more audio segments received from a user device to be authenticated. The one or more video frames may be generated using a camera of the user device and include a representation of a user of the user device. The audio segments may include a representation of a voice of the user. User authentication 128 may transmit a request to machine-learning (ML) core process 132 to process the video and/or audio. ML core process 132 may monitor one or more machine-learning models configured to provide the services of the communication network (e.g., user authentication, communication session management, resources, content generation, natural language processing, automated communication such as a bot or the like, etc.). ML core process 132 may train new machine-learning models, retrain (or reinforce) existing machine-learning models, delete machine-learning models, and/or the like. Since ML core process 132 manages the operations of a variety of machine-learning models, each request to ML core process 132 may include an identification of a particular machine-learning model, a requested output, or the like to enable ML core process 132 to route the request to an appropriate machine-learning model or instantiate and train a new machine-learning model. Alternately, ML core process 132 may analyze data to be processed that is included in the request to select an appropriate machine-learning model configured to process data of that type.

If ML core process 132 cannot identify a trained machine-learning model configured to process the request, then ML core process 132 may instantiate and train one or more machine-learning models configured to process. For instance, ML core process 132 may instantiate a first machine-learning model configured to process the one or more video frames (e.g., such as a deep neural network, concurrent neural network, etc.) and a second machine-learning model configured to process the one or more audio segments (e.g., such as a recurrent neural network like a long-short term memory, or the like). Other operations of communication network 120 may be facilitated by other types of machine-learning models such as, but not limited to classifiers (e.g., regression models, support vector machines, statistical models etc.), clustering models, generative models (e.g., such as large language models, generative adversarial networks, autoencoders, etc.), etc.

ML core process 132 may select one or more machine-learning models based on characteristics of the data to be processed and/or the output expected. ML core process 132 may then use feature extractor 136 to generate training datasets for the new machine-learning models (e.g., other than those models configured to perform feature extraction such as some deep learning networks, etc.). Feature extractor 136 may define training dataset using historical session data 140. Historical session data 140 may store features from previous communication sessions. In some instances, the previous communication sessions may not involve the user of the first user device or the user of the second user device. Previous communication sessions may include manually and/or procedurally generated data generated for use in training machine-learning models. Historical session data 140 may not store any information associated with healthcare providers or patients. Alternatively, historical session data 140 may store features extracted from communication session involving the user of the first user device, the user of the second user device, and/or other patients and/or other healthcare providers.

Feature extractor 136 may extract video features to train the machine-learning model that will be configured to process video data and feature extractor 136 may extract video features to train the machine-learning model that will be configured to process the audio segments from historical session data 140. Feature extractor 136 may include a search function (e.g., such as procedural search, Boolean search, natural language search using a large language model assisted search, or the like) to enable ML core process 132, an administrator, or the like to search for particular datasets within historical session data 140. Feature extractor 136 may aggregate the extracted features into one or more training datasets usable to train a respective machine-learning model of the one or more machine-learning models. The training datasets may include training datasets for training the machine-learning models, training datasets to validate an in-training or trained machine-learning model, training datasets to test a trained machine-learning model, and/or the like. The one or more training datasets may be passed to ML core process 132, which may manage the training process.

Feature extractor 136 may pass the one or more training datasets to ML core process 132 and ML core process 132 may initiate a training phase for the one or more machine-learning models. The one or more machine-learning models may be trained using supervised learning, unsupervised learning, self-supervised learning, or the like. The one or more machine-learning models may be trained for a predetermined time interval, a predetermined quantity of iterations, until one or more target accuracy metrics have exceeded a corresponding threshold function (e.g., accuracy, precision, area under the curve, logarithmic loss, F1 score, weighted human disagreement rate, cross entropy, mean absolute error, mean square error, etc.), user input, combinations thereof, or the like. Once trained, ML core process 132 may validate and/or test the trained machine-learning models using additional training datasets. The machine-learning models may also be trained at runtime using reinforcement learning.

Once trained the machine-learning models, ML core process 132 may manage the operation of the one or more machine-learning models (stored with other machine-learning models in machine-learning models 148). ML core process 132 may direct feature extractor 136 to define feature vectors from received data (e.g., such as the video data and/or audio segments, etc.). For example, feature extractor 136 may define a first feature vector from the video data and/or a second feature vector from the audio segments. Feature extractor 136 may define other feature vectors to process other data using machine-learning models of machine-learning models 148 to provide other resources of communication network 120. ML core process 132 may use ML model selector 144 to identify a first machine-learning model configured to process the first feature vector (e.g., the video data) and identify a second machine-learning model configured to process the second feature vector (e.g., the audio segments). For example, the video data may be processed using a machine-learning model configured to extract features associated with a representation of a user (e.g., such as a face, upper body, etc.) and/or features associated with a background. In some instances, the machine-learning model may use monocular depth estimation to generate a depth map that includes a value for each pixel of an input image corresponding to a predict distance of the pixel in the environment from the camera that captured the image.

User authentication 128 may use the depth map to distinguish pixels corresponding to the user from pixels corresponding to the background (e.g., based on the pixels representing the user being generally closer than pixels representing the background). User authentication 128 may then determine relative differences in distances between one or more pixels to determine a relative depth of one or more facial features. The relive differences in distances may be obfuscated features that may be used to determine whether the user represented by the video data is authenticated by comparing the obfuscated features to obfuscated features of an authenticated user.

The second machine-learning model may process the second feature vector to derive obfuscated features associated with the audio segments, the second machine-learning model may be configured to identify pitch, tone, speech velocity, pause frequency and length, diction, accent, language, etc.) of the audio segment. The obfuscated features may be numerical values that can be compared to historical obfuscated features of an authenticated user to determine if the user associated with the obfuscated features is the same user as the user associated with the historical obfuscated features.

User authentication 128 may determine, based on the obfuscated features (derived from the first feature vector and/or the second feature vector), whether a user corresponds to an authenticated user by comparing the obfuscated features to obfuscated features previously generated for that user or to obfuscated features previously generated for a plurality of authenticated users. If user authentication 128 does not have previously generated obfuscated features for a particular user for a comparison (e.g., this is the first time the user has accessed communication network 120), then user authentication 128 may request additional information from the user to verify the user's identity (e.g., such as, but not limited to, an image from an independent source such as webpage of the healthcare provider or a driver's license, information from an authenticated user, identifying information from an associated health system (e.g., clinic, office, hospital, etc. affiliated with the user), combinations thereof, or the like.

Alternatively, communication network 120 may request that a user for which no previously generated obfuscated features are stored by communication network 120, register with communication network 120 prior to a first communication session involving the user. The user may provide one or more images, an audio sample, and any of the aforementioned additional information to verify an identify of the user and generate obfuscated features for the user. Communication network 120 may generate a user profile for the user that includes the obfuscated features, an identification of the user (e.g., such as a name, title, medical specialty, and/or the like), and an indication as to whether the user is authenticated (e.g., the identity of the user is verified). If so, communication network 120 may use generate obfuscated features during each communication session involving the user and compare them to the user profile for the user. If the obfuscated features match, then communication network 120 may authenticate that the user connected to this communication session is the same user that has registered with the communication network 120 and has been verified.

In some instances, user authentication 128 may also use device and/or network information such as, but not limited to, IP address, MAC address, a username, a device identifier, a hardware fingerprint (e.g., an identification of hardware components of the corresponding user device), a software fingerprint (e.g., an identification of software components of the corresponding user device), a packet size, an internet service provider, a location of the corresponding user device, combinations thereof. By comparing the obfuscated features to previously generated obfuscated features, user authentication 128 may determine that the current user of a user device correspond to a same user that previously accessed the communication system.

User authentication 128 may transmit a notification to communication session manager 124 indicating whether a user of a user device corresponds to an authenticated user. If the user is authenticated, then the communication session may continue. If the user is not authenticated, user communication session manager 124 may request additional identifying information (e.g., such as token, public/private key, or other secure information) or may terminate the connection associated with the unauthenticated user.

Figure 2:
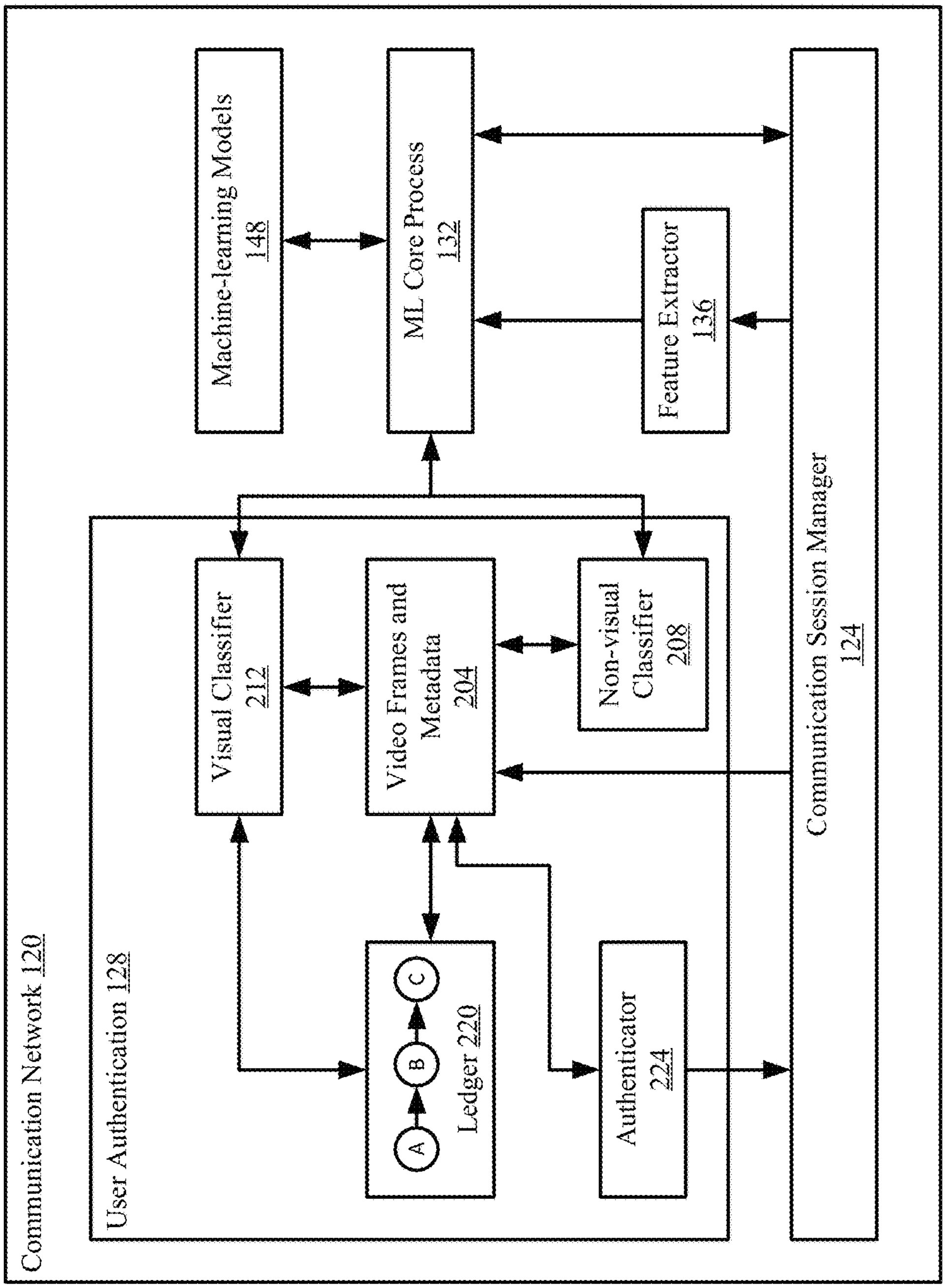
FIG. 2 illustrates a block diagram of a user authentication component of a communication system configured to authenticate a user connected to a communication session according to aspects of the present disclosure.

FIG. 2 illustrates a block diagram of a user authentication component of a communication system configured to authenticate a user connected to a communication session according to aspects of the present disclosure. User authentication 128 may use various features derived from a user device connected to a communication session to authenticate a user of the user device. For example, user authentication 128 may use biometric data (e.g., facial imaging, audio segments, etc.), object detection (e.g., objects within an environment of the user as represented within an image), network pattern analysis (e.g., using IP addresses, MAC addresses, user device identifiers, user device characteristics, user device locations, etc.), combinations thereof, or the like to generate a likelihood that the current user corresponds to a same user Communication session manager 124 may transmit a request to authenticate a user to video frames and metadata 204 of user authentication 128. The request may include one or more video frames in which at least one video frame includes a representation of the user to be authenticated, one or more audio segments including a sample of the user's voice, metadata (e.g., including, but not limited to, one or more identifiers associated with the user such as a name, username, passcode, password, encryption keys, and/or the like; an identification of the user device operated by the user; an identification of characteristics of the user device such as hardware components and/or software installed thereon; network information such as IP address, MAC address, internet service provider, etc.; a location of the user device; an identification of when the user device connected to the communication session relative to the start time of the communication session; configuration information associated with the communication session if supplied by the user; a purpose for which the communication session is established; an identifier associated with other user devices connected to the communication session and/or an indication as to whether the other user devices have ever connected to same communication session as the user device in the past; combinations thereof; or the like). The request may be transmitted before a communication session, at the start of a communication session, anytime during the communication session, and/or after the communication session.

Video frames and metadata 204 may use an identifier associated with the user (e.g., an identity of the user provided by the user such as a name or username, etc.) to identify a user profile associated with the identifier. The user profile may include a set of authentication features corresponding to features captured or received by communication network during one or more previous instances in which the user associated with the identifier connected to a communication session. For example, the set of authentication features may include features associated a visual representation of the user (e.g., facial features, depth maps, etc.), objects within an environment during one or more previous communication sessions, audio features (e.g., features associated with a representation of the user's voice or speech, etc.) from one or more previous communication sessions, metadata from one or more previous communication sessions, and/or the like.

User profiles may be stored in ledger 220 as linked datasets. The first time a user connects to communication network 120, the user may register with communication network 120 by providing a user identifier (e.g., such as a name, username, etc.) and a title (e.g., patient, doctor or other healthcare provider, healthcare administrator, nurse, aide, parent or guardian, etc.). User authentication 128 may authenticate the user using one or more independent data sources (e.g., using a license or other credential, third-party guarantor, an administrator or other party from a healthcare system (e.g., healthcare provider's office, hospital, etc.), an administrator or other party from an insurance company, another healthcare provider, or the like), a token or access code provided to the user through an independent source (e.g., such as mail, email, phone call, text message, an application via push notifications, another user, or the like), combinations thereof, or the like. Once authenticated, user authentication 128 may generate a new linked dataset for the user. The new linked dataset may include a single node with the information provided by the user during registration (e.g., the set of authentication features) and an indication that the user is authenticated.

Any feature of a node for which a correspondence or relation can be established with one or more other features based on the features having a same value may be referred to as an exact feature. Examples of exact features include, but are not limited to, a name or username, IP address, device identifiers, a location, etc. may be obfuscated using a first encryption algorithm. The first encryption algorithm may be a hashing function (e.g., a Secure Hash Algorithm (SHA), Cyclic Redundancy Check (CRC), a Message Digest algorithm such as MD5, etc.). Hash functions are configured to generate a same output (e.g., a hash value) for a same input (e.g., a feature, etc.). The output cannot be used to recover or rederive the input. As a result, a first hash value can be compared to a second hash value. If the first hash value matches the second hash value, then feature input to generate the first hash value matches the feature input to generate the second hash value. By hashing features of the node that can be exactly matched, user authentication 128 can determine that information received from a user matches a node of a linked dataset without using or revealing any identifying features. In some instances, the encryption keys for the first encryption algorithm may be deleted upon encryption to prevent any device or individual, including communication network 120, from accessing identifying information stored in the linked datasets.

The features of a node that are unlikely to exactly match to a corresponding feature received from communication network 120 (referred to herein as non-exact features) may be obfuscated using a second encryption algorithm, salting, feature selection, combination thereof, or the like. For example, the time in which a user connects to communication sessions relative to the start time of the communication session may vary inconsequentially between communication sessions. The user may connect approximately one minute thirty-two seconds before a first session and two minutes and fourteen seconds before a second communication session. It is unlikely, though not impossible, that the user joins each communication at the exact same time.

User authentication 128 may use a second obfuscation algorithm to encrypt non-exact features. The non-exact features may be decrypted to enable a comparison with received features and re-encrypted to prevent unauthorized access. In some instances, the second encryption algorithm may be different from the first encryption algorithm. In those instances, the encryption keys (public and/or private keys, etc.) of the first encryption algorithm can be deleted to prevent the exact features of the node from being decrypted without preventing the non-exact features from being decrypted for comparison.

Salting the non-exact features may include modifying a value of a non-exact feature to prevent with a constant value that prevents the value of the feature from being usable to derive an identity of a user. User authentication 128 may convert non-exact features into a numerical value (for those that are not already a numerical value) and multiple the value by the constant value. The constant value may be derived based on a random number generator (RNG) and the checksum of the node. The constant value may vary for each node and for each linked dataset to prevent a leaked constant value from providing access to the non-exact features of an entire user profile. The constant value may be generated when the node and checksum is generated. The constant value may be stored separately (e.g., in a secure store or the like) in an encrypted and/or unencrypted state.

Feature selection is a process for selecting from a larger set of features. User authentication 128 may use feature selection to select a subset of features from a class of features and remove the remain features in the class. The subset of features may be too few to identify the user and/or rederive the class of features (e.g., using interpolation, regression, etc.). For example, a depth map of a face may be used to reconstruct a representation of the face that can be used for facial recognition to identify a user. User authentication 128 may use feature selection to select one or more features from the depth map useable to determine an accurate match with another depth map. The remaining features of the depth map be deleted to prevent the depth map from being reconstructed or usable to reconstruct a representation of the user.

Exact features of a node may be annotated with a value or flag indicating the feature is an exact feature. Non-exact features of a node may be annotated with a value or flag indicating the feature is a non-exact feature. Exact features may be encrypted using the first encryption algorithm. Non-exact features may be obfuscated using one or more of the second encryption algorithm, salting, feature selection, combinations thereof, or the like. For example, user authentication 128 may use each of the second encryption algorithm, salting, and feature selection to obfuscate non-exact features. The features may be annotated by user authentication 128, a machine-learning model of machine-learning models 148, user input, or the like. For example, a machine-learning model may classify each feature as being an exact feature or non-exact feature.

The node may also be encrypted (e.g., encrypting both the encrypted exact features and the obfuscated non-exact features) using a third encryption algorithm to further secure linked dataset. The first encryption algorithm, second encryption algorithm, and the third encryption algorithm may be the same algorithm or different algorithms. Each node may be encrypted using a different third encryption algorithm and/or using different encryption keys.

Each time the user access communication network 120, user authentication 128 may receive new information associated with the user that may be used to augment the data stored in the linked dataset. Some of the new information may include the same information previously provided by the user (e.g., such as the user identifier, etc.). The new information may be merged with the existing information of the linked dataset. For example, when the user connects to communication network 120, communication network 120 may first authenticate the user (e.g., determine if current information received from the user corresponds to the information of the linked dataset associated with the user). Once authenticated, user authentication 128 may generate a new node of the linked dataset associated with the user. The new node may merge information of the previously generated node with the new node (e.g., generating a new set of authentication features). Any information from the previous node for which there is no conflicting information in the new information may be preserved. Any information from the new information for which there is no conflicting information in the previous node may be added to the new node. Conflicting information (e.g., any data type in which a value exists in both the previous node and the new information) may be combined (e.g., summed, averaged, weighted averaged, aggregated, etc.) in a manner based on the data type of the conflicting information. For example, facial information (e.g., depth maps, etc.) may be combined by normalizing the values of a depth map and averaging the values based on the quantity of nodes of the linked dataset for which a depth map is stored plus one (e.g., accounting for the depth map of the new information) creating an average depth map of the user. Averaging the depth maps may improve the accuracy of user authentication 128 when determining whether a depth map corresponds to a user by reducing the weight of minor variations in individual depth maps. For another example, IP address may be aggregated to maintain the IP address stored in previous nodes and the new IP address. User authentication 128 may also store a timestamp in the new node corresponding to when the new node was generated and/or when the user accessed communication network 120.

The new node may be linked to the immediately previously generated node of the linked dataset creating the linked nature of the linked dataset. The most recently generate node may represent the combine information associated with the user. The links (e.g., pointers, or the like) may be usable to trace information received and/or derived from the user over time The linked nodes enable user authentication 128 to analyze user information during previous instances in which the user accessed the communication session.

The nodes of a linked dataset may be immutable (e.g., non-editable, etc.). For example, the nodes of a linked dataset and/or the linked dataset may be stored in read-only memory, write-protected memory, or the like. In some instances, each node may be associated with one or more checksums usable to determine if a node has been edited or deleted. If user authentication 128 determines that a linked dataset has been modified (e.g., edited and/or partially deleted) based on the checksums, user authentication 128 may delete the linked dataset and force the user associated with the now-deleted linked dataset re-register with communication network 120. Alternatively, user authentication 128 may delete nodes of a linked dataset that have been modified. For example, if user authentication 128 determines that a current node (e.g., the most recently generated node) has been edited based on a comparison of a checksums, user authentication 128 may delete nodes starting with the most recent node moving backwards in time until a node is identified that has not been edited.

In some instances, ledger 220 may be a digital ledger (e.g., such as a blockchain, or the like), which may provide a secure way to store persistent information associated with the user. In other instances, the user profiles may be stored as other data structures.

Video frames and metadata 204 may segment the information from communication session manager 124 into a first dataset, which may be usable to authenticate facial and other visual features associated with the user, and a second dataset, which may be usable to authenticate non-visual features associated with the user. Video frames. For example, the first data set may include the video frames and the metadata, etc. and the second dataset may include audio segments and the metadata. Video frames and metadata 204 may pass the first dataset to visual classifier 212 with an identification of the user profile associated with the user and the second dataset to non-visual classifier 208 with the identification of the user profile.

Non-visual classifier 208 may include one or more processes and/or machine-learning models configured to predict, based on the second dataset and/or any features derived from the second dataset, whether the user of the user device is authenticated (e.g., the user of the user device corresponds to a known user that is authorized to operate communication sessions with other user devices).

Non-visual classifier 208 may communicate with ML core process 132 to derive additional features from the second dataset. For example, non-visual classifier 208 may request a machine-learning model to process audio segments. ML core process 132 may instantiate, train, and execute machine-learning models in machine-learning models 148 to process the audio segments and return a result to non-visual classifier 208. In the example of audio segments, ML core process 132 may instantiate and train a recurrent neural network (e.g., such as, but not limited to, a long-short term memory model) if such a model is not present in machine-learning models 148. ML core process 132 may then execute the recurrent neural network to derive features from the second dataset (e.g., text from words represented by the audio segment, semantic analysis of the words, speech pattern analysis, etc.). The recurrent neural network may return output features and/or an output feature vector including one or more of text from of words represented by the audio segment, a predicted semantic representation of the words, a predicted intent of the user, speech pattern features (e.g., an identification rate of speech, audio frequencies associated with speech indicative, an identification of syntax and/or diction used by the user, frequency and/or length of pauses, speech disfluencies, etc.), an identification of spoken language, etc.

Non-visual classifier 208 may process the second dataset, metadata, and output features to generate a set of comparable features. Non-visual classifier 208 may generate a prediction indicative of whether the user of the user device corresponds to an authenticated user (e.g., the user is the individual the user is claiming to be) by comparing the set of comparable features to the set of authentication features. If the most recent node of the linked dataset is encrypted using a third encryption algorithm, user authentication 128 may decrypt the most recent node to obtain the set of authentication features. Since exact features of the set of authentication features may be encrypted using the first encryption algorithm, user authentication 128 may encrypt the exact features of the set of comparable features using the same first encryption algorithm used to encrypt the most recently generated node of linked dataset of the user profile. Alternatively, user authentication 128 may decrypt the portions of the set of authentication features encrypted by the first encryption algorithm (if ledger 220 stores the decryption keys). If the non-exact features of the set of authentication features are obfuscated (e.g., salted, encrypted using a second encryption algorithm, reduced via feature selection, etc.), then user authentication 128 may obfuscate the non-exact features of the set of visual features to enable a comparison between the set of authentication features and the set of visual features.

Each feature of the set of comparable features may be weighted based on a degree in which the feature can be associated with a single user. For example, features associated with access credentials are likely to be associated with a single user (e.g., it is unlikely that two different users would have the same access credentials). Features associated with the user device (e.g., IP address, MAC address, hardware/software components installed thereon, etc.) may correspond with a medium degree of predictiveness (e.g., it is possible that multiple users may operate a same device, a same user may operate multiple devices or upgrade a device, etc.). Features associated with some names may correspond with a low predictiveness as some names may be common within a community (e.g., "John Smith," etc.).

Non-visual classifier may generate a value between 0 and 1 for each feature of the set of comparable features based on the degree in which a feature matches a corresponding feature of the set of authentication features, with 1 being an exact match and 0 being no match. The value may be adjusted by multiplying the value by the weight assigned to the feature.

In some instances, non-visual classifier 208 may derive an overall value based on the values assigned to each feature of the set of comparable features (e.g., average of the values, weighted average of the values using the weights associates features, sum of the values, etc.). Alternatively, non-visual classifier 208 may derive an overall value based on the quantity of features with a value that is greater than a threshold. Non-visual classifier 208 may generate a prediction of whether the user of the user device is the same user as the user associated with the user profile (e.g., an authenticated user, etc.) based on the overall value. The prediction may be a binary value such as a value of true (e.g., user of the user device is the same user as the user associated with the user profile) or false (e.g., user of the user device is not the same user as the user associated with the user profile). Alternatively, the prediction may be the overall value. The overall may also be indicative of a confidence of the prediction. A high overall value and a low overall value (e.g., such as an overall value close to 0 or 1) may correspond to a confidence that the prediction is accurate.

In some instances, when user authentication 128 cannot identify a user profile associated with the user, user authentication 128 may search ledger 220 for one or more user profiles that are a closest match to the set of comparable features. Non-visual classifier 208 may then predict a likelihood that the user corresponds to a same user associated with the closest matching user profile based the comparison (e.g., based on how close the closest matching user profile is to the set of comparable features based on the aforementioned comparison process). If non-visual classifier 208 predicts that the user is the same user associated with the closest user profile and the user profile corresponds to an authenticated user, then non-visual classifier 208 may output an indication that the user is authenticated. If non-visual classifier 208 predicts that the user is not the same user associated with the closest user profile or the user profile corresponds to a non-authenticated user, then non-visual classifier 208 may output an indication that the user is not authenticated.

Video frames and metadata 204 may pass the first dataset to visual classifier 212. Visual classifier 212 may perform similar processes as non-visual classifier 208 using the first dataset. For example, visual classifier 212 may communicate with ML core process 132 to derive features from the first dataset. For example, visual classifier 212 may request the processing of the video frames and/or the metadata. ML core process 132 may instantiate, train, and execute machine-learning models stored in machine-learning models 148 to process the video frames and return a result to visual classifier 212. The result may include, but is not limited to, output features characterizing the video frames, one or more predictions of objects represented in the video frames (e.g., from a classifier or a classification layer, etc.), depth maps, boundary boxes, masks, kernels, segmentations, and/or the like.

ML core process 132 may execute a first one or more machine-learning models (e.g., such as a convolutional neural network, etc.) to process the video frames. Each machine-learning model of the one or more machine-learning models may be trained to generate a different output. One machine-learning model may be trained to execute monocular depth estimation to produce depth maps of the video frames. Another machine-learning model may be trained to identify objects represented in the video frame, etc. For example, the one or more first machine-learning models may be configured to generate a depth map of a video frame (e.g., using a monocular depth estimation model, etc.). The depth map may include, for each pixel of the video frame, a predicted distance of a point in the environment represented by the pixel to the camera that captured the video frame. A second machine-learning model may be used to process the metadata, the video frames, and/or the output of the first one or more machine-learning models derive additional features, generate predictions (e.g., classification, etc.), or the like.

Visual classifier 212 may process the first dataset, the metadata, and the output from the first one or more machine-learning models to generate a set of visual features that can be compared to features of the user profile associated with the user (e.g., the set of authentication features corresponding to the most recently generated node of the linked dataset of the user profile). If the most recently generated node of the linked dataset is encrypted using a third encryption algorithm, user authentication 128 may decrypt the most recent node to obtain the set of authentication features. Since exact features of the set of authentication features may be encrypted using the first encryption algorithm, visual classifier 208 may encrypt the exact features of the set of visual features using the same first encryption algorithm used to encrypt the most recently generated node of linked dataset of the user profile. Alternatively, user authentication 128 may decrypt the portions of the set of authentication features encrypted by the first encryption algorithm (if ledger 220 stores the decryption keys). If the non-exact features of the set of authentication features are obfuscated (e.g., salted, encrypted using a second encryption algorithm, reduced via feature selection, etc.), then user authentication 128 may obfuscate the non-exact features of the set of visual features to enable a comparison between the set of authentication features and the set of visual features.

The type of comparisons performed may be based on the second dataset and the output from the first one or more machine-learning models. The results of some comparisons may be a Boolean value (e.g., true if the value of a data type of the second dataset and/or the output from the first one or more machine-learning models matches the value of a data type present in the set of authentication features and false if the value of a data type of the second dataset and/or the output from the first one or more machine-learning models does not match the value of a data type present in the set of authentication features). For example, the output from the first one or more machine-learning models may include an object identified (e.g., data type) as a diploma (e.g., value) hanging on the wall behind the user. If the set of authentication features includes a data type of identified object with a value of diploma, then an exact match is identified.

The results of some comparisons may be a value corresponding to a degree in which the value of a data type of the second dataset and the output from the first one or more machine-learning models matches a value of the corresponding data type of the set of authentication features. For example, visual classifier may use a distance algorithm (e.g., nearest neighbors, etc.), or the like.

In some instances, each feature of the set of visual features may be weighted based on a degree in which the feature can be associated with a single user. For example, features associated the visual appearance of the user may be highly predictive of a single user. Features associated with objects detected within a video frame (e.g., art, coffee cup, blinds, a diploma, etc.) may be less predictive of a single user (e.g., different users may use the same coffee cup, etc.). The weights may be assigned by a machine-learning model, visual classifier 212, user input, or the like.

Visual classifier 212 may generate a value between 0 and 1 for each feature of the set of visual features based on the degree in which a feature matches a corresponding feature the set of authentication features. The value may be adjusted by multiplying the value by the weight assigned to the feature.

In some instances, visual classifier 212 may derive an overall value based on the values assigned to each feature of the first dataset, metadata, and output from the first one or more machine-learning models. The overall value may be based on an average of the values, weighted average of the values using the weights associates features, sum of the values, etc. Alternatively, visual classifier 212 may derive an overall value based on the quantity of features with a value that is greater than a threshold. Visual classifier 212 may generate a prediction of whether the user of the user device is the same user as the user associated with the user profile (e.g., an authenticated user, etc.) based on the overall value. The prediction may be a binary value such as a value of truc (e.g., user of the user device is the same user as the user associated with the user profile) or false (e.g., user of the user device is not the same user as the user associated with the user profile). Alternatively, the prediction may be the overall value. The overall value may also be indicative of a confidence of the prediction. A high overall value and a low overall value (e.g., such as an overall value close to 0 or 1) may correspond to a confidence that the prediction is accurate.

For example, visual classifier 212 may use ML core process 132 to generate a depth map from a video frame. Visual classifier 212 may segment the depth map to identify the pixels of video frame representing the user. For example, visual classifier 212 may use thresholds to identify contiguous pixels that correspond to a similar distance based on thresholds (e.g., such as contiguous pixels that are within 25 mm distance variation. The contiguous pixels that have similar distances likely correspond to pixels representing a same object. Alternatively, ML core process 132 may return a segmented depth map with annotations identifying pixels corresponding to particular objects of interest including the pixels representing the user. Visual classifier 212 may identify one or more pixels of the pixels representing the user with the smallest depth value and generate normalized depth values based on the smallest. For example, visual classifier may determine the difference between each depth value of the pixels representing the user and the smallest depth value. The resulting normalized depth map may reduce the effect of variations between depth maps when the user is sitting closer or further from the camera.

The normalized depth map may be stored in the set of visual features and used to compare to a corresponding depth map of the user profile (e.g., represented in the set of authenticated features of the most recent node of the linked dataset of the user profile). Since the depth maps may still have some variations (e.g., resulting from that machine-learning model that generated the depth map, lighting, etc.), visual classifier 212 may use a distance matching algorithm (e.g., nearest neighbors, etc.) or a machine-learning model to determine if the depth map matches the depth map of the user profile (e.g., as previously described).

In some instances, such as when privacy and/or security is not a concern, visual classifier 212 may use a facial recognition classifier. The facial recognition classifier may include one or more facial-recognition machine-learning models configured to output an identity of a face represented in an input image. The one or more facial-recognition machine-learning models may be trained using a set of images that include a representation of a face of a set of users. Each image may include a label corresponding to an identifier of the user (e.g., a name, user identifier, username, etc.) represented in the image and/or an indication of whether the user represented in the image is an authenticated user. The output of the one or more machine-learning models for a given input image may include the identifier of the user represented in the input image and/or the indication whether the user represented in the image is an authenticated user. The one or more facial-recognition machine-learning models may be configured to output just the indication of whether the user represented in the image is an authenticated user to protect the identification of the user from being accessed. Visual classifier 212 may store the output of the one or more facial-recognition machine-learning models with the set of visual features as a feature usable with other features to authenticate the user.

In some instances, visual classifier 212 may use one or more machine-learning models to compare the set of visual features to the set of authentication features. The machine-learning model (e.g., a clustering model, classifier, and/or the like) may identify relationships between the features the set of visual features and/or the set of authentication features that be indicative of that the user hiding or obfuscating identifying information. For example, visual classifier 212 may use a machine-learning to generate a set of expected features based on the set of authenticated features and features associated with the communication session (e.g., the time of the communication session, the stated location of the user and the location of the user determined by the data packets transmitted by the user device, whether the locations are daylight at the time, current weather at the locations, etc.). The machine-learning model may correlate the set of visual features with the set of expected features to determine if there are inconsistencies in the set of visual features and/or the set of expected features. For example, a video frame may include a representation of a portion of a window behind the user. The set of expected features may indicate that the location of the user (e.g., determined by the data packets) is in a place that should be daylight. The machine-learning model may use the set of visual features (e.g., the processed portion of the video frames) to determine if the video frame (e.g., the representation of the window) is consistent with the expectation of daylight. For another example, the machine-learning model may determine that the stated location of the user is different from an expected location (e.g., based on previous communication session and/or from data packets transmitted by the user device, etc.). The machine-learning model may identify inconsistencies in the features that may be indicative that the current user of the user device is not the same as the user associated with the user profile.

In some instances, user authentication 128 may remove one or more values of the normalized depth map of the user profile to prevent the normalized depth map from being usable to reproduce the facial features of the user. User authentication 128 may use the shape of the user (e.g., based on the portion of the depth map representing the user as previously described) to select one or more normalized depth values usable for comparison. Increasing the quantity of normalized depth values to compare may increase the accuracy of the comparison while also increasing the risk that the stored data may be able to recreate the representation of the user. The quantity of normalized depth values that are to be retained may be determined by user authentication 128, a machine-learning model (e.g., configured to determine the location of a minimum quantity of normalized depth values that can be compared to identify a match), user input, and/or the like.

In some instances, when user authentication 128 cannot identify a user profile associated with the user, user authentication 128 may search ledger 220 for one or more user profiles that are a closest match to the set of comparable features. Visual classifier 208 may then predict a likelihood that the user corresponds to a same user associated with the closest matching user profile based the comparison (e.g., based on how close the closest matching user profile is to the features of the set of visual features based on the aforementioned comparison process). If visual classifier 212 predicts that the user is the same user associated with the closest user profile and the user profile corresponds to an authenticated user, then visual classifier 212 may output an indication that the user is authenticated. If visual classifier 212 predicts that the user is not the same user associated with the closest user profile or the user profile corresponds to a non-authenticated user, then visual classifier 212 may output an indication that the user is not authenticated.

The results of the comparison (e.g., the individual values, overall value, and/or the predictions) from visual classifier 212 and non-visual classifier 208 may be passed to authenticator 224. Authenticator may generate an indication as whether the user is authenticated or not authenticated. For example, authenticator 224 may indicate the user is authenticated when both the visual classifier 212 and non-visual classifier 208 generate an authenticated prediction (e.g., indicating the user is as the user associated with the authenticated user profile). Alternatively, authenticator 224 may weigh the results and generate the indication from the weighted results. The weighted results may result in an indication of authenticated even when visual classifier 212 or non-visual classifier 208 generated a prediction of not authenticated. For example, the facial comparison (e.g., via depth maps or the like) of visual classifier 212 may be weighted higher than audio-based authentication used by non-visual classifier.

If authenticator 224 determines that the user is authenticated, then authenticator 224 may cause user authentication 128 to update the user profile stored in ledger 220. User authentication 128 may generate a new set of authenticated features by merging the set of comparable features and the set of visual features with the set of authenticated features of the most recently generated node of the linked dataset of the user profile (as previously described). The new set of authenticated features may be processed by remove some values (e.g., such values of a depth map that may be used to recreate a representation of the user as previously described), encrypt values that can be exactly matched using the first encryption algorithm, and/or the like. User authentication 128 may then link the most recently generated node of the linked dataset to a new node configured to store the new set of authenticated features. User authentication 128 may then generate checksums for the new node and encrypt the new node using a second encryption algorithm.

If authenticator 224 determines that the user is not authenticated, then authenticator 224 may cause communication session manager 124 to terminate the communication session and/or report the user to the healthcare provider, healthcare system, authorities, and/or the like.

Communication session manager 124 may authenticate users in real time (e.g., when the user connects to communication network 120, etc.) during one or more times during a communication session or as a batch process (e.g., at any time after the communication session).

If a user cannot be authenticated (e.g., is not associated with a known user profile or is associated with unauthorized user profile), the communication session involving the user may be terminated and the user may be reported. For example, if the user is claiming to be a user associated with a user profile and the user cannot be authenticated using the user profile (e.g., the user is a different person from the person the user is claiming to be), authenticator 224 may cause the communication session to be terminated and the user to be reported to user associated with the user profile (e.g., the healthcare provider), the healthcare system or office associated with the user profile, an insurance company, a medical licensing board, and/or the like.

In some examples, authenticator 224 may generate a collusion map. A collusion map may include interconnected nodes that identify relationships between healthcare provider, healthcare systems, and patients, and/or other parties that associated with communication network 120. Each node of the collusion map may represent a user (and/or user profile) and be linked to one or more other nodes based on one or more relationships. Examples of features usable to link users and/or user profiles include, but are not limited to, familial relationship, shared education (e.g., college, med school, residency, etc.), shared address (e.g., same office), shared cities of residence (e.g., past or present), shared social contacts, common business contacts (e.g., including past or present employment histories, ownership interests, etc.), medical specialties, common patients, common healthcare providers, referrals (e.g., healthcare provider that refers a patient to a second healthcare provider may cause the first healthcare provider to be linked to the second healthcare provider, common insurance (e.g., accepted insurance for healthcare services, malpractice insurance, etc.), etc. The features may be weighted based on a degree in which a common feature indicates an association between two users. The weights may be assigned based on user input, a machine-learning model (e.g., configured to detect relationships between features such as an autoencoder, etc.), previous iterations of authenticator 224, combinations thereof, or the like. Each link may be assigned a score indicating the degree in which a node is related to another to a connected node. The score may be derived based on the quantity of common features and the corresponding weights of those features.

The collusion map may be presented visually as a three-dimensional graph model. The nodes may include any graphical representation. Nodes may be represented as having a single link (e.g., corresponding to an aggregate quantity of common features of the connected nodes) or as set of links each representing common features. The links between nodes may be represented with a numerical value and/or thickness indicative of degree in which the nodes are related (e.g., determined based on the weights and the quantity of common features). Links can be unidirectional or bidirectional. In some instances, links may include other identifiers (symbols, colors, etc.) indicating the type of relationship linking the two nodes.

The collusion map may be searched upon detecting fraudulent activity such as unauthorized access to the communication network. For example, during a communication session, authenticator 224 may detect that the healthcare provider connected to the communication session does not match the features of the corresponding user profile indicating that healthcare provider is being impersonated by another user. A healthcare provider may be impersonated duc to identify theft or due to fraud (e.g., the healthcare provider is unlawfully authorizing another individual to pose as the healthcare provider). Authenticator 224 may use the collusion may to identify a first node associated with the healthcare provider (e.g., the node of the user profile being impersonated). Authenticator 224 may then identify those nodes connected to the first node with a score that is greater than a threshold. Authenticator 224 may identify those user profiles (and the users associated therewith) that have a substantial relationship with the impersonated user profile so as to be a similar target for impersonation (e.g., via identity theft or the like) or be colluding with the healthcare provider to commit fraud (e.g., a co-conspirator, etc.). Authenticator 224 may report the unauthorized access to the healthcare provider and to one or more other parties (e.g., the healthcare system associated with the healthcare provider, a licensing authority, other authorities, etc.). In some examples, authenticator 224 may temporarily mark the node associated with the healthcare provider as suspicious and prevent any user alleging to be user of the node from connecting to communication sessions until it can be determined whether it is identity theft or fraud. If the unauthorized access is the result of is identity theft, a new user profile may be established for the user to enable the user to access communication network 120. If the unauthorized access is the result of is fraud, then the user may be banned from accessing the communication network. A user profile may be generated using the information obtained before the unauthorized access was detected to prevent the user from access the communication network under a different name.

Authenticator 224 may also authenticate information received from user devices to determine that the information is not fraudulent, corrupt, malicious, etc. Authenticator 224 may receive files (e.g., such as text, audio, images, video, electronic health records, etc.) as well as communications transmitted over the communication session. For some files, authenticator 224 may use checksums, error correction codes, signatures, tokens, etc. to determine if the files received from user devices are corrupt, includes errors, include malicious data or code, etc. For some files, such as those intended to facilitate a particular false diagnosis or treatment (e.g., such as for opioids, etc.), insurance or billing fraud, etc., authenticator 224 may analyze the contents of the files. For example, authenticator 224 may use user input (e.g., manual review), machine-learning models, statistical models, combinations thereof, or the like to detect falsified data. For example, authenticator 224 may use a combination of clustering (e.g., identify relationships or patterns in features extracted from communication sessions, etc.) and comparisons to records associated with the users connected to the communication session to detect false or incorrect data.

In some instances, authenticator 224 may also use a natural language understanding machine-learning model (e.g., such as a large language model, etc.) configured to analyze voice communications transmitted over the communication network for malicious activity. For example, the natural language understanding machine-learning model may be configured to identify keywords or phrases spoken during the communication session by the healthcare provider and/or other users. The natural language understanding machine-learning model or another machine-learning model may identify combinations of keywords, patterns, trends of keywords spoken, etc. that may be associated with malicious activity.

Authenticator 224 may update the collusion map upon detection falsified or fraudulent data, malicious activity detect from speech, and/or any other detected malicious activity associated with a particular user. The collusion map may be used to identify a network of users associated with the particular user that may be colluding with the particular user (e.g., also associated with malicious activity). The network of users may be identified based on the degree in which users of the collusion map are related to the particular user or to a user related to the particular user, etc. Each user of the network may be marked for further monitoring, reporting, etc. and/or terminated from the communication network.

Figure 3:
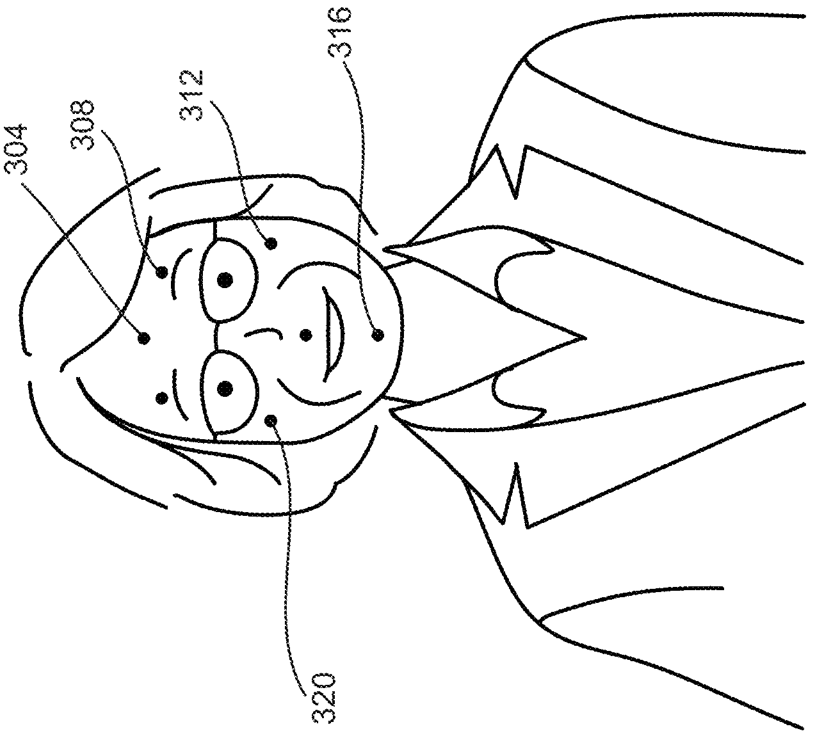
FIG. 3 illustrates features derived from biometric data and usable to determine if the biometric data matches biometric data of an authenticated user according to aspects of the present disclosure.

FIG. 3 illustrates features derived from biometric data and usable to determine if the biometric data matches biometric data of an authenticated user according to aspects of the present disclosure. Visual classifier 212 may process video frames that include a representation of a user to determine if the user corresponds to an authenticated user. In some instances, if security is not a concern, visual classifier 212 may use one or more facial-recognition machine-learning models to identify the user using facial recognition. The facial-recognition machine-learning models (e.g., convolution neural networks, etc.) may be trained to receive an input image with a representation of a user and output an identification of the user or an indication of whether the user represented in the image is authenticated user. Since the facial-recognition machine-learning models may be trained using labeled images, it may be possible for some personal identifiable information to be accessible (e.g., such as training images that faces of users, labels corresponding to names or user identifiers, features corresponding to characteristics of the user, etc.). Visual classifier 212 may increase data security and minimize the likelihood of leaking features that can be used to derive identifiable information (or other sensitive information associated with the user) by using minimized depth maps along with other features to match a user with a record associated with an authenticated user. Visual classifier 212 can determine that the user is an authenticated user without identifying the user or using information that could be usable to identify the user.

Generating the minimized depth map may include generating a depth map from a video frame received from a camera of a user device (e.g., using monocular depth estimation by a machine-learning model of machine-learning models 248, etc.). The depth map may include, for each pixel of the video frame, a predicted distance of a position within the environment represented by the pixel and the camera that captured the video frame. Video classifier 212 may receive the depth map and identify particular regions of the depth map that are likely to correspond to the user. For example, a user is likely to sit between two to four feet from the camera. Video classifier 212 may use distance thresholds to remove portions of the depth map that correspond to the background (e.g., such as distances values that are greater than a threshold distance of 6 feet, etc.) and portions that of the depth map that are too close to the camera and unlikely to correspond to the user's face (e.g., such as distance values that are less than a threshold distance of 1 foot, etc.). The distance thresholds may be defined by previous iterations of visual classifier 212, user input, or the like and may be set to any values usable to eliminate the portions of the depth map that do not correspond to the user.

Alternatively, visual classifier 212 may use another machine-learning model to perform pattern analysis to identify regions of the image likely to correspond to the user's face. Pattern analysis may look for particular shapes or patterns of pixels that may correspond to a user. Alternatively, visual classifier 212 may use a ratio of depth values to identify the pixels that correspond to the user. By measuring the ratio of depth values, visual classifier 212 can distinguish relative distances within the environment to identify a user from other objects represented in the video frame.

Visual classifier 212 may segment the portion of the pixels representing the user into one or more facial regions such as an upper (e.g., including forehead, etc.), lower (e.g., including mouth, chin, etc.), central (e.g., including eyes, nose, etc.), left (e.g., including the right eye, right check, etc.), right (e.g., including the left eye, left cheek, etc.), etc. The one or more regions may be identified using object detection (e.g., via a convolutional neural network, etc.) or based on one or more facial landmarks. For examples, pixels associated with a nose, a representing central facial feature, may be identified based on smaller distance values than surrounding pixels. Facial regions may then be defined based on locations relative to the pixels associated with the nose.

Visual classifier 212 may then select one or more distance values from depth map from each facial region. For instance, visual classifier 212 may identify pixel 304 and 308 corresponding to upper region pixels 312 and 320 representing a middle region, and pixel 316 representing a lower region, etc. Visual classifier 212 may determine, through multiple iterations of user authentication, user input, a machine-learning model, etc. a quantity of distance values to select for each region to enable generating a minimized depth map that can be used to identify a user with a target confidence. The target confidence may correspond to a likelihood that a depth map from a video frame that matches a minimized depth map from a user profile is associated with a same user as the user that caused the user profile to be generated. The target confidence need not be 100% because visual classier 212 and non-visual classifier 208 may use other features to authenticate the user (e.g., such objects within the video frame, non-visual features, etc.). Visual classifier 212 may define the target confidence based on a quantity of other features being used to authenticate the user. Visual classifier 212 may determine the quantity of distance values and for each facial regions based on the target confidence.

In some examples, the portion of the depth map representing the face may be segmented into four regions (upper left, upper right, lower left, and lower right) based on the pixels representing a nose (e.g., a central facial feature identifiable based on having lower distance values than surrounding facial features, etc.). Visual classifier 212 may select one or more distance values from each region. Visual classifier 212 may store, with each distance value, an identification of the region from which the distance value was obtained and an approximate location of the pixel relative to the face of the user (e.g., the approximate location on the user that the pixel of the depth map represents).

Visual classifier 212 may normalize the distance values using other distance values. For example, visual classifier 212 may select one distance value from the distance values representing the face of the user. In some instances, visual classifier 212 may select the largest distance value, the smallest distance value, the median distance value, the average distance value, etc. Visual classier 212 may then calculate, for each distance value of the minimized depth map, the absolute delta from the selected distance value. Alternatively, or additionally, the visual classifier 212 may determine the absolute data of each distance value relative to each other distance value. The normalized pixel values may prevent changes in the distance between the user and the camera from affecting the authentication. The normalized pixel values of a same user may be subject to smaller variations between communication session. For example, if a user sits three feet from the camera during one communication session and two feet from the camera during a second communication session, the depth map and minimized depth map will likely be unchanged (or change insubstantially) because the relative distances between distance values will likely remain the same in each communications session.

FIG. 4 illustrates a flowchart of an example process authenticating users connected to a communication system according to aspects of the present disclosure. At block 404, a computing device (e.g., a component of a communication network, a server, other device, etc.) may receive one or more video frames from a video communication session between a first user device and a second user device. The first user device may be operated by a healthcare provider and the second user device may be operated by patient. One or more other devices may also be connected to the communication session operated by users that may be affiliated with the healthcare provider (e.g., such as an administrator, another healthcare provider, nurse, aide, etc.) or the patient (e.g., such a guardian, nurse, aide, etc.). The computing device may authenticate any user connected to the communication session. In some instances, the computing device may authenticate each user other than the patient (to preserve the patient's privacy and/or to prevent gathering or storing sensitive information associated with the patient). In other instances, the computing device may authenticate each user connected to the communication session.

The computing device may authenticate users using the one or more video frames (at least one of which may include a representation of a user). The first user device and the second user device may each include a camera facing the user of the first user device and the second user device. The camera may capture a single video frame (e.g., an image or the like), periodically capture video frames, or continuously capture video frames as part of the communication session. The computing device may use the video frames to authenticate the user.

At block 408, the computing device may extract, from at least one video frame, a set of features associated with the user of the first user device. The features may correspond to characteristics of the video frame and/or the communication from which the video frame was received (e.g., such as characteristics of the user device, network information associated with the user device, etc. as previously described). In some examples, the set of features correspond to a preprocessed version of the video frame in which portions of the video frame that do not represent a human person are omitted.

At block 412, the computing device may execute a neural network using the set of features to generate a first depth map of the user of the first user device. Alternatively, the computing device may execute the neural network using the one or more video frames. The first depth map may be a depth map that defines a distance value for each pixel of the video frame that corresponds to an estimated distance of the point in the environment represented by the pixel is from the camera that captured the video frame. The depth map may provide a representation of a face of the user represented in the video frame. The depth map may be normalized by deriving the relative differences between a distance value and one or more other distance values. For example, the computing device may select the smallest depth value (e.g., the pixel representing a point estimated to be closest to the camera) and deriving, for each depth value the absolute difference from the smallest depth value. By normalizing the depth map, the computing device can derive a version of the depth map that is unaffected by the distance of the user from the camera.

The computing device may authenticate the user of the first user device based on matching the first depth map with a second depth map associated with an authenticated user. The computing device may store user profiles associated with authenticated and non-authenticated users. The user profile may store a sequence of nodes as a linked data structure (e.g., digital ledger such as a blockchain, linked list, etc.), where each node stores a minimized depth map (e.g., minimized version of a normalized depth map) and linked to previously generated node. The computing device may compare the first depth map to the depth map of the first node in the sequence of nodes (e.g., the most recently generated node). If the two depth maps match (e.g., determined using a distance algorithm, a machine-learning model, etc.), computing device may determine that the user of the first user device is the same user as the user associated with the user profile. If the user profile corresponds to an authenticated user, then the user of the first user device may be determined to be an authenticated user.

The computing device may compare the first depth map to multiple depth maps (each being associated with a different user profile) and identify the second depth map as the depth map of the multiple depth map that is the closest match to the first depth map (as previously described). If match (between the first depth map and the closets matching depth map) is greater than threshold (e.g., as determined by the distance algorithm, confidence value or the like from the machine-learning model, etc.), then the closest matching depth map is determined to be the second depth map.

The computing device may generate a new node in the sequence of nodes that includes a depth map generated from the first depth map and the depth map that was stored in the first node. The new node may become the new most recently generated node and used during subsequent comparisons involving the user profile. Since the user profile is updated each time a match is detected, the depth maps of the user profile may more accurately correspond to the user over time (e.g., increasing accuracy and reducing false positives and false negatives).

The minimized depth map may be generated by generating a depth map (or normalized depth map) and systematically removing distance values until a minimum quantity of distance values remain. The minimized depth map may be generated to prevent storing personal identifiable information or other information that may be sensitive to the user associated with the user profile. Removing distance values from a depth map may increase a likelihood that a first depth map from more than one user may match a same minimized depth map. The computing device may use user input, previous iterations of the authentication process, one or more machine-learning models (e.g., cluster-based models, autoencoders, etc.), feature importance, etc.) to determine a minimum quantity of distance values to authenticate a particular user based on comparing one or more other features associated with the user (e.g., such as other objects in the video frame, voice-pattern analysis of the user, user device characteristics, network characteristics associated with the user device such as an IP address, etc.). Generally, the larger the quantity of other features available to compare, the fewer depth values needed to authenticate the user (relative to a predetermined minimum quantity of depth values). For example, the first depth map may be matched to the second depth map (e.g., the minimum depth map), which as a result of the removal of one or more depth values may also be matched to depth maps of one or more other users. The computing device may increase the accuracy of the matching by also matching an IP address of the first user device to ensure that the user of the first user device is likely the user associated with the authenticated user profile. The computing device may use any feature that can be extracted from the first user device during the communication session (e.g., video frames, characteristics of the first user device characteristics, characteristics of a network connection of the first user device, user credentials, cryptographic keys, tokens, codewords, etc.).

By matching the first depth map to the (minimized) second depth map, the computing device can authenticate users without storing or exposing personal identifiable information (e.g., such as, but not limited to, images or other representations of the user).

The computing device may generate, in response to authenticating the user, a third depth map by merging the first depth map with the second depth map. The third depth map may be used to authenticate the user of the first user device during a subsequent video communication session involving the first user. The first depth map may be merged with the second depth map calculating an updated distance value for each distance value of the second depth map based on the first depth map. The second depth map (e.g., the minimized depth map) may include a second set of distance values with each distance value being associated with an approximate location (e.g., coordinate location, facial region, or the like) of a representation of the user (e.g., such as a face of the user, etc.) associated with the second depth map. The computing device may identify a first set of distance values from the first depth map associated with a same location as the distance values of the second depth map (e.g., each distance value of the first set of distance values may be a distance value associated with a same location as a corresponding distance value of the second depth map). The computing device may then define a third set of distance values with each distance value of the third set of distance values derived based on a distance value of the second set of distance values and the corresponding distance value of the first set of distance values (e.g., the distances values of the first set of distance values and the second set of distance values representing a same location of the representation of the user). The third set of distance values may be derived based on deriving an aggregation of the distance values (e.g., appending the distance values, adding the distance values, etc.), average of the distance values, median of the distance values, mode of the distance values, another statistical merging process, combinations thereof, or the like. In some instances, the computing device may store the distance values each set of distance values evaluated to enable generating update sets of distance values each time the user is authenticated.

The third depth map (e.g., the third set of distance values) may be used to generate a new node of the matched user profile usable to authenticate the user during the communication session and/or during a subsequent communication session. When the user of the first user device connects to a subsequent communication session, the computing device may generate a new depth map and compare the new depth map to the third depth map of the user profile. Each time the user profile is matched to a depth map of a user, the user profile may be updated generating a new node and a new (minimized) depth map. Over time the depth map of the user profile may be less subject to small variations in distances, increasing the accuracy of the depth map.

If the user of the first user device does not match the second depth map, then the computing device may update a collusion map associated with the user. The collusion map may represent a degree in which users of the communication network are related based on common characteristics. The more related two users are the stronger the link between those users in the collusion map. The collusion map may be used to identify a risk of malicious activity within the communication network induced by users (e.g., such as fraud, identity theft, misrepresentation, etc.). If the computing device detects that a first user is impersonating a healthcare provider, then the risk of malicious activity associated with users associated with the first user and/or the impersonated healthcare provider may increase (e.g., as it may be more likely that colleagues of the first user may be impersonating healthcare providers or enabling others to do so). The collusion map may trace the relationships between users of the communication network in real time to detect networks users associated with potentially malicious activity. The computing device may determine to terminate access to the communication network to users associated with malicious activity within the collusion map, report users to licensing authority or other authorities, report users to patients or healthcare systems, etc.

Figure 5:
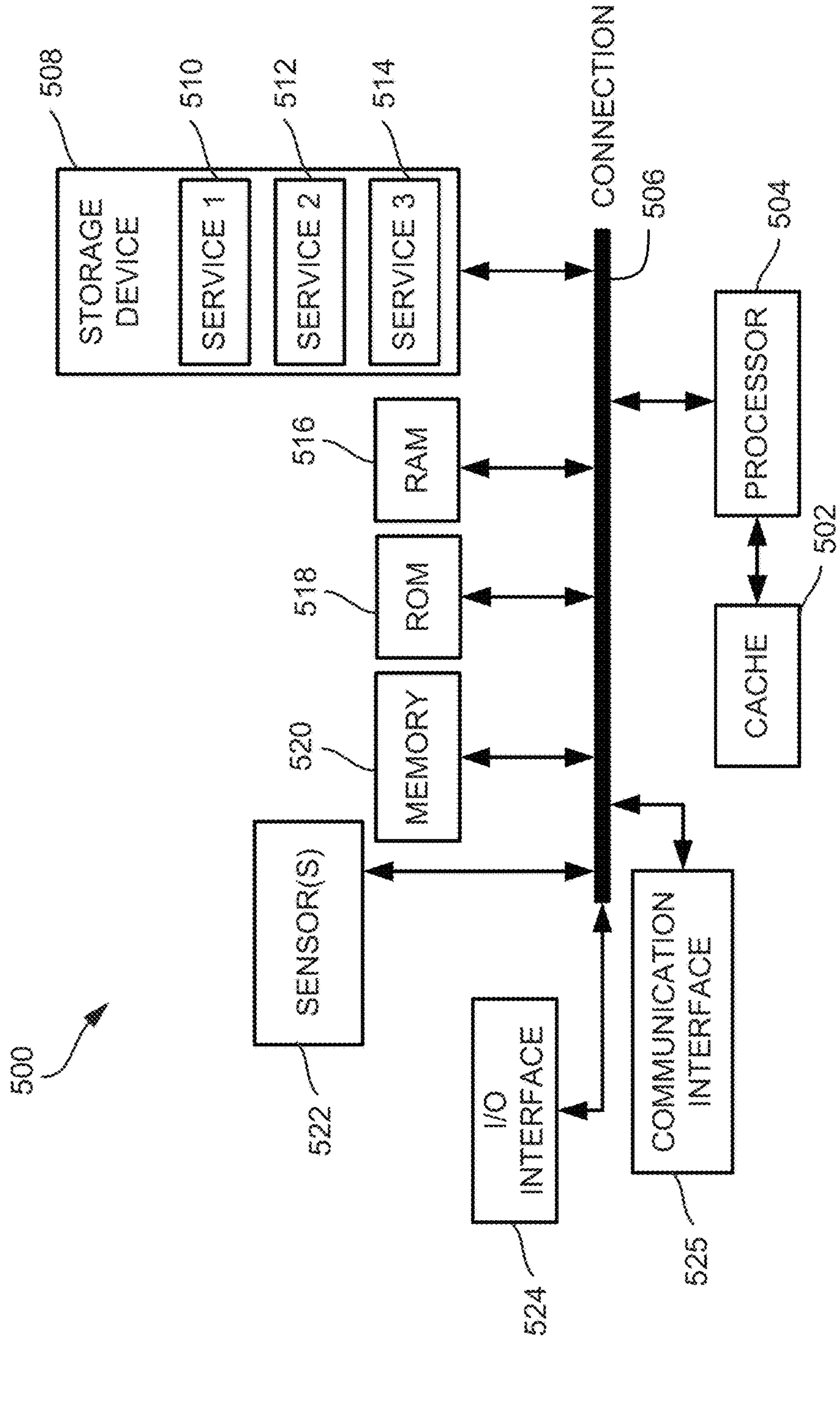
FIG. 5 illustrates an example computing device architecture of an example computing device that can implement the various techniques described herein according to aspects of the present disclosure.

FIG. 5 illustrates an example computing device according to aspects of the present disclosure. For example, computing device 500 can implement any of the systems or methods described herein. In some instances, computing device 500 may be a component of or included within a media device. The components of computing device 500 are shown in electrical communication with each other using connection 506, such as a bus. The example computing device architecture 500 includes a processor (e.g., CPU, processor, or the like) 504 and connection 506 (e.g., such as a bus, or the like) that is configured to couple components of computing device 500 such as, but not limited to, memory 520, read only memory (ROM) 518, random access memory (RAM) 516, and/or storage device 508, to processing unit 510.

Computing device 500 can include a cache 502 of high-speed memory connected directly with, in close proximity to, or integrated within processor 504. Computing device 500 can copy data from memory 520 and/or storage device 508 to cache 502 for quicker access by processor 504. In this way, cache 502 may provide a performance boost that avoids delays while processor 504 waits for data. Alternatively, processor 504 may access data directly from memory 520, ROM 517, RAM 516, and/or storage device 508. Memory 520 can include multiple types of homogenous or heterogeneous memory (e.g., such as, but not limited to, magnetic, optical, solid-state, etc.).

Storage device 508 may include one or more non-transitory computer-readable media such as volatile and/or non-volatile memories. A non-transitory computer-readable medium can store instructions and/or data accessible by computing device 500. Non-transitory computer-readable media can include, but is not limited to magnetic cassettes, hard-disk drives (HDD), flash memory, solid state memory devices, digital versatile disks, cartridges, compact discs, random access memories (RAMs) 525, read only memory (ROM) 520, combinations thereof, or the like.

Storage device 508, may store one or more services, such as service 1 510, service 2 512, and service 3 514, that are executable by processor 504 and/or other electronic hardware. The one or more services include instructions executable by processor 504 to: perform operations such as any of the techniques, steps, processes, blocks, and/or operations described herein; control the operations of a device in communication with computing device 500; control the operations of processing unit 510 and/or any special-purpose processors; combinations therefor; or the like. Processor 504 may be a system on a chip (SOC) that includes one or more cores or processors, a bus, memories, clock, memory controller, cache, other processor components, and/or the like. A multi-core processor may be symmetric or asymmetric.

Computing device 500 may include one or more input devices 522 that may represent any number of input mechanisms, such as a microphone, a touch-sensitive screen for graphical input, keyboard, mouse, motion input, speech, media devices, sensors, combinations thereof, or the like. Computing device 500 may include one or more output devices 524 that output data to a user. Such output devices 524 may include, but are not limited to, a media device, projector, television, speakers, combinations thereof, or the like. In some instances, multimodal computing devices can enable a user to provide multiple types of input to communicate with computing device 500. Communications interface 526 may be configured to manage user input and computing device output. Communications interface 526 may also be configured to managing communications with remote devices (e.g., establishing connection, receiving/transmitting communications, etc.) over one or more communication protocols and/or over one or more communication media (e.g., wired, wireless, etc.).

Computing device 500 is not limited to the components as shown if FIG. 5. Computing device 500 may include other components not shown and/or components shown may be omitted.

The following examples illustrate various aspects of the present disclosure. As used below, any reference to a series of examples is to be understood as a reference to each of those examples disjunctively (e.g., "Examples 1-4" is to be understood as "Examples 1, 2, 3, or 4").

Example 1 is a method comprising: receiving one or more video frames from a video communication session between a first user device and a second user device, wherein at least one video frame of the one or more video frames includes a representation of a user of the first user device; extracting, from the at least one video frame, a set of features associated with the user of the first user device; executing a neural network using the set of features to generate a first depth map of the user of the first user device; authenticating the user of the first user device based on matching the first depth map with a second depth map associated with an authenticated user; and generating, in response to authenticating the user, a third depth map by merging the first depth map with the second depth map, the third depth map being usable to authenticate the user of the first user device during a subsequent video communication session involving the user.

Example 2 is the method of example(s) 1, wherein the neural network generates the first depth map using monocular depth estimation to determine a distance between one or more positions of the user and a camera that captured the one or more video frames.

Example 3 is the method of example(s) 1-2, wherein the first depth map includes a set of data values associated with a facial feature of the user.

Example 4 is the method of example(s) 1-3, wherein the third depth map is stored in read-only memory.

Example 5 is the method of example(s) 1-4, wherein the third depth map is linked to the second depth map in a digital ledger.

Example 6 is the method of example(s) 1-5, wherein authenticating the user is further based on one or more audio segments from the video session and associated with the user.

Example 7 is the method of example(s) 1-6, wherein authenticating the user is further based on metadata of the video communication session.

Example 8 is a system comprising of one or more processor and a non-transitory computer-readable medium storing instructions that when executed by the one or more processors cause the one or more processors to perform the methods of any of example(s) 1-7.

Example 9 is a non-transitory computer-readable medium storing instructions that when executed by the one or more processors cause the one or more processors to perform the methods of any of example(s) 1-7.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored in a form that excludes carrier waves and/or electronic signals. Examples of a non-transitory medium may include, but are not limited to, a magnetic disk or tape, optical storage media such as compact disk (CD) or digital versatile disk (DVD), flash memory, memory, or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

Some portions of this description describe examples in terms of algorithms and symbolic representations of operations on information. These operations, while described functionally, computationally, or logically, may be implemented by computer programs or equivalent electrical circuits, microcode, or the like. Furthermore, arrangements of operations may be referred to as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In some examples, a software module can be implemented with a computer-readable medium storing computer program code, which can be executed by a processor for performing any or all of the steps, operations, or processes described.

Some examples may relate to an apparatus or system for performing any or all of the steps, operations, or processes described. The apparatus or system may be specially constructed for the required purposes, and/or it may comprise a general-purpose computing device selectively activated or reconfigured by a computer program stored in memory of computing device. The memory may be or include a non-transitory, tangible computer readable storage medium, or any type of media suitable for storing electronic instructions, which may be coupled to a bus. Furthermore, any computing systems referred to in the specification may include a single processor or multiple processors.

While the present subject matter has been described in detail with respect to specific examples, it will be appreciated that those skilled in the art, upon attaining an understanding of the foregoing, may readily produce alterations to, variations of, and equivalents to such embodiments. Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter. Accordingly, the present disclosure has been presented for purposes of example rather than limitation, and does not preclude the inclusion of such modifications, variations, and/or additions to the present subject matter as would be readily apparent to one of ordinary skill in the art.

For clarity of explanation, in some instances the present disclosure may be presented as including individual functional blocks including functional blocks comprising devices, device components, steps or routines in a method embodied in software, or combinations of hardware and software. Additional functional blocks may be used other than those shown in the figures and/or described herein. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Individual examples may be described herein as a process or method which may be depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed but may have additional steps not shown. A process may correspond to a method, a function, a procedure, a subroutine, a subprogram, etc. When a process corresponds to a function, its termination can correspond to a return of the function to the calling function or the main function.

Processes and methods according to the above-described examples can be implemented using computer-executable instructions that are stored or otherwise available from computer-readable media. Such instructions can include, for example, instructions and data which cause or otherwise configure a general-purpose computer, special purpose computer, or a processing device to perform a certain function or group of functions. Portions of computer resources used can be accessible over a network. The computer executable instructions may be, for example, binaries, intermediate format instructions such as assembly language, firmware, source code, etc.

Devices implementing the methods and systems described herein can include hardware, software, firmware, middleware, microcode, hardware description languages, or any combination thereof, and can take any of a variety of form factors. When implemented in software, firmware, middleware, or microcode, the program code or code segments to perform the necessary tasks (e.g., a computer-program product) may be stored in a computer-readable or machine-readable medium. The program code may be executed by a processor, which may include one or more processors, such as, but not limited to, one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A processor may be a microprocessor; conventional processor, controller, microcontroller, state machine, or the like. A processor may also be implemented as a combination of computing components (e.g., a combination of a DSP and a microprocessor, a plurality of microprocessors, one or more microprocessors in conjunction with a DSP core, or any other such configuration). Accordingly, the term "processor," as used herein may refer to any of the foregoing structure, any combination of the foregoing structure, or any other structure or apparatus suitable for implementation of the techniques described herein. Functionality described herein also can be embodied in peripherals or add-in cards. Such functionality can also be implemented on a circuit board among different chips or different processes executing in a single device, by way of further example.

In the foregoing description, aspects of the disclosure are described with reference to specific examples thereof, but those skilled in the art will recognize that the disclosure is not limited thereto. Thus, while illustrative examples of the disclosure have been described in detail herein, it is to be understood that the inventive concepts may be otherwise variously embodied and employed, and that the appended claims are intended to be construed to include such variations. Various features and aspects of the above-described disclosure may be used individually or in any combination. Further, examples can be utilized in any number of environments and applications beyond those described herein without departing from the broader spirit and scope of the disclosure. The disclosure and figures are, accordingly, to be regarded as illustrative rather than restrictive.

The various illustrative logical blocks, modules, circuits, and algorithm steps described in connection with the embodiments disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present application.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or media devices of the computing platform. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the claim.

The invention claimed is:

1. A method comprising:

receiving one or more video frames from a video communication session between a first user device and a second user device, wherein at least one video frame of the one or more video frames includes a representation of a user of the first user device;

extracting, from the at least one video frame, a set of features associated with the user of the first user device;

executing a neural network using the set of features to generate a first depth map of the user of the first user device;

authenticating the user of the first user device based on matching the first depth map with a second depth map associated with an authenticated user; and generating, in response to authenticating the user, a third depth map by merging the first depth map with the second depth map, the third depth map being usable to authenticate the user of the first user device during a subsequent video communication session involving the user.

2. The method of claim 1, wherein the neural network generates the first depth map using monocular depth estimation to determine a distance between one or more positions of the user and a camera that captured the one or more video frames.

3. The method of claim 1, wherein the first depth map includes a set of data values associated with a facial feature of the user.

4. The method of claim 1, wherein the third depth map is stored in read-only memory.

5. The method of claim 1, wherein the third depth map is linked to the second depth map in a digital ledger.

6. The method of claim 1, wherein authenticating the user is further based on one or more audio segments from the video communication session and associated with the user.

7. The method of claim 1, wherein authenticating the user is further based on metadata of the video communication session.

8. A system comprising:

one or more processors; and a non-transitory computer-readable medium storing instructions that when executed by the one or more processors, cause the one or more processors to perform the operations including:

receiving one or more video frames from a video communication session between a first user device and a second user device, wherein at least one video frame of the one or more video frames includes a representation of a user of the first user device;

extracting, from the at least one video frame, a set of features associated with the user of the first user device;

executing a neural network using the set of features to generate a first depth map of the user of the first user device;

authenticating the user of the first user device based on matching the first depth map with a second depth map associated with an authenticated user; and generating, in response to authenticating the user, a third depth map by merging the first depth map with the second depth map, the third depth map being usable to authenticate the user of the first user device during a subsequent video communication session involving the user.

9. The system of claim 8, wherein the neural network generates the first depth map using monocular depth estimation to determine a distance between one or more positions of the user and a camera that captured the one or more video frames.

10. The system of claim 8, wherein the first depth map includes a set of data values associated with a facial feature of the user.

11. The system of claim 8, wherein the third depth map is stored in read-only memory.

12. The system of claim 8, wherein the third depth map is linked to the second depth map in a digital ledger.

13. The system of claim 8, wherein authenticating the user is further based on one or more audio segments from the video communication session and associated with the user.

14. The system of claim 8, wherein authenticating the user is further based on metadata of the video communication session.

15. A non-transitory computer-readable medium storing instructions that when executed by one or more processors, cause the one or more processors to perform operations including:

receiving one or more video frames from a video communication session between a first user device and a second user device, wherein at least one video frame of the one or more video frames includes a representation of a user of the first user device;

extracting, from the at least one video frame, a set of features associated with the user of the first user device;

executing a neural network using the set of features to generate a first depth map of the user of the first user device;

authenticating the user of the first user device based on matching the first depth map with a second depth map associated with an authenticated user; and generating, in response to authenticating the user, a third depth map by merging the first depth map with the second depth map, the third depth map being usable to authenticate the user of the first user device during a subsequent video communication session involving the user.

16. The non-transitory computer-readable medium of claim 15, wherein the neural network generates the first depth map using monocular depth estimation to determine a distance between one or more positions of the user and a camera that captured the one or more video frames.

17. The non-transitory computer-readable medium of claim 15, wherein the first depth map includes a set of data values associated with a facial feature of the user.

18. The non-transitory computer-readable medium of claim 15, wherein the third depth map is stored in read-only memory.

19. The non-transitory computer-readable medium of claim 15, wherein the third depth map is linked to the second depth map in a digital ledger.

20. The non-transitory computer-readable medium of claim 15, wherein authenticating the user is further based on one or more audio segments from the video communication session and associated with the user.

* * * * *